United States Patent
Patel et al.

(10) Patent No.: US 9,723,380 B2
(45) Date of Patent: Aug. 1, 2017

(54) METHOD OF AND SYSTEM FOR AUTOMATICALLY ADJUSTING AIRFLOW AND SENSORS FOR USE THEREWITH

(71) Applicant: EcoVent Corp., Magnolia, NJ (US)

(72) Inventors: Dipul Patel, Revere, MA (US); Nicholaus Ray Lancaster, Mineral Wells, TX (US)

(73) Assignee: ecoVent Corp., Boston, MA (US)

( * ) Notice: Subject to any disclaimer, the term of this patent is extended or adjusted under 35 U.S.C. 154(b) by 235 days.

(21) Appl. No.: 14/264,161

(22) Filed: Apr. 29, 2014

(65) Prior Publication Data

US 2015/0130631 A1 May 14, 2015

Related U.S. Application Data

(60) Provisional application No. 61/955,297, filed on Mar. 19, 2014, provisional application No. 61/902,939, filed on Nov. 12, 2013.

(51) Int. Cl.
*G08C 19/22* (2006.01)
*H04Q 9/00* (2006.01)
(Continued)

(52) U.S. Cl.
CPC .......... *H04Q 9/00* (2013.01); *F24F 11/0001* (2013.01); *F24F 11/001* (2013.01);
(Continued)

(58) Field of Classification Search
CPC .............. F24F 11/0001; F24F 11/0012; F24F 2011/0068; F24F 2011/0072; Y02B 30/78
See application file for complete search history.

(56) References Cited

U.S. PATENT DOCUMENTS

| | | |
|---|---|---|
| 4,538,134 A | 8/1985 | Carey |
| 4,864,269 A | 9/1989 | Priebe |

(Continued)

FOREIGN PATENT DOCUMENTS

| | | |
|---|---|---|
| WO | WO-2012/013964 A1 | 2/2012 |
| WO | WO-2013/040657 A1 | 3/2013 |

OTHER PUBLICATIONS

International Search Report and Written Opinion issued by the U.S. Patent and Trademark Office as International Searching Authority for International Application No. PCT/US2014/065011 dated May 27, 2015 (17 pages).

*Primary Examiner* — Omeed Alizada
(74) *Attorney, Agent, or Firm* — Wilmer Cutler Pickering Hale and Dorr LLP

(57) ABSTRACT

A method of and system for automatically adjusting airflow and sensors for use therewith are disclosed. A sensor assembly includes a first face on an opposite side of the sensor assembly relative to a second face. The assembly includes an electrical plug on the first face and an electrical outlet on the second face. The electrical outlet is of a same type that is complimentary to the electrical plug on the first face. The assembly includes a sensor for sensing a value of an environmental variable in a space and a sensor communication system for transmitting and receiving information. A sensor system includes a plurality of sensor assemblies disposed in a building. Each sensor assembly includes a sensor for sensing a value of an environmental variable of the space within which the sensor is placed. The system determines gradient values for the sensed environmental variable.

4 Claims, 28 Drawing Sheets

(51) Int. Cl.
   *G01N 19/10*    (2006.01)
   *G01C 19/00*    (2013.01)
   *F24F 11/00*    (2006.01)
   *G01N 29/00*    (2006.01)
   *G01L 7/08*     (2006.01)

(52) U.S. Cl.
   CPC ........ *F24F 11/006* (2013.01); *F24F 11/0012* (2013.01); *F24F 11/0034* (2013.01); *F24F 11/0076* (2013.01); *G01C 19/00* (2013.01); *G01N 19/10* (2013.01); *F24F 2011/0013* (2013.01); *F24F 2011/0026* (2013.01); *F24F 2011/0027* (2013.01); *F24F 2011/0042* (2013.01); *F24F 2011/0058* (2013.01); *F24F 2011/0068* (2013.01); *F24F 2011/0072* (2013.01); *G01L 7/08* (2013.01); *G01N 29/00* (2013.01); *Y02B 30/78* (2013.01)

(56) References Cited

U.S. PATENT DOCUMENTS

| | | |
|---|---|---|
| 5,271,558 A | 12/1993 | Hampton |
| 5,303,767 A | 4/1994 | Riley |
| 5,364,024 A | 11/1994 | Lin |
| 6,648,750 B1 | 11/2003 | Wiseman |
| 6,692,349 B1 | 2/2004 | Brinkerhoff et al. |
| 7,168,627 B2 | 1/2007 | Kates |
| 7,347,774 B2 | 3/2008 | Aronstam et al. |
| 7,554,437 B2 | 6/2009 | Axelsen |
| 7,656,664 B2 | 2/2010 | Ye et al. |
| 7,693,809 B2 | 4/2010 | Gray |
| 8,061,417 B2 | 11/2011 | Gray |
| 8,244,405 B2 | 8/2012 | Kao et al. |
| 8,289,160 B1 | 10/2012 | Billman |
| 8,290,628 B2 | 10/2012 | Yeo |
| 8,374,729 B2 | 2/2013 | Chapel et al. |
| 8,467,734 B2 | 6/2013 | Schubert |
| 8,979,622 B2 | 3/2015 | Casey |
| 9,322,569 B2 | 4/2016 | Scharf et al. |
| 2004/0159713 A1 | 8/2004 | Schmidt et al. |
| 2006/0063522 A1* | 3/2006 | McFarland ............ H04Q 9/00 455/423 |
| 2008/0041969 A1 | 2/2008 | Nathan |
| 2008/0188173 A1 | 8/2008 | Chen et al. |
| 2008/0242212 A1 | 10/2008 | El-Galley et al. |
| 2008/0311842 A1* | 12/2008 | Alston ................ F24F 11/0012 454/361 |
| 2009/0002146 A1 | 1/2009 | Lin |
| 2009/0065595 A1 | 3/2009 | Kates |
| 2009/0174547 A1 | 7/2009 | Greene et al. |
| 2010/0012737 A1 | 1/2010 | Kates |
| 2010/0033024 A1 | 2/2010 | Crucs |
| 2010/0083731 A1* | 4/2010 | Hedtke ................ G01L 27/007 73/1.57 |
| 2010/0163633 A1 | 7/2010 | Barrett et al. |
| 2010/0288468 A1 | 11/2010 | Patel et al. |
| 2011/0009045 A1 | 1/2011 | Beckley et al. |
| 2011/0198404 A1 | 8/2011 | Dropmann |
| 2012/0182698 A1 | 7/2012 | Langels et al. |
| 2012/0201179 A1 | 8/2012 | Das et al. |
| 2012/0239773 A1 | 9/2012 | Blustein et al. |
| 2012/0275526 A1 | 11/2012 | Hughes |
| 2013/0245842 A1 | 9/2013 | Lu et al. |
| 2013/0303554 A1 | 11/2013 | Klein et al. |
| 2014/0005809 A1 | 1/2014 | Frei et al. |
| 2014/0025805 A1 | 1/2014 | Apte et al. |
| 2014/0032003 A1 | 1/2014 | Chapel et al. |

* cited by examiner ent of the invention.

METHOD OF AND SYSTEM FOR AUTOMATICALLY ADJUSTING AIRFLOW AND SENSORS FOR USE THEREWITH

CROSS-REFERENCE TO RELATED APPLICATIONS

This application claims the benefit under 35 U.S.C. §119(e) to U.S. Provisional Patent Application No. 61/902,939, entitled Method of and System for Automatically Adjusting Airflow, filed on Nov. 12, 2013, and U.S. Provisional Patent Application No. 61/955,297, entitled Method of and System for Automatically Adjusting Airflow, filed on Mar. 19, 2014, the contents of each of which are incorporated by reference herein.

BACKGROUND OF THE INVENTION

Field of Invention

The invention generally relates to controlling one or more environmental conditions in a structure, and, more specifically, to techniques for automatically adjusting airflow from a common environmental control system into one or more spaces of a structure.

Description of Related Art

Heating, ventilation, and air conditioning (HVAC) systems are designed to maintain the health and safety of building conditions by regulating environmental variables such as temperature and humidity. Some buildings have multiple spaces or zones, the environmental conditions of which are controlled by multiple, independent, HVAC systems. For example, a building may have several floors, and each floor may have its own HVAC system.

In addition, an HVAC system can be designed to provide air flow to each space or zone (e.g., a room) within the building. In such systems, a central control unit that it part of the HVAC system can control air flow in parts of the HVAC distribution system to selectively supply air to one space or zone but not another. For example, a main air supply duct can have two branches in which each branch leads to a different room. Each of the branches can have a damper that prevents air flow through the branch. If the HVAC system detects that one room requires cooling air while the other does not, it will close the damper to the room not requiring cooling and open the damper to the room that requires cooling.

BRIEF SUMMARY OF THE INVENTION

Under one aspect of the invention, a method of and system for automatically adjusting airflow and sensors for use therewith are disclosed.

Under another aspect of the invention, a sensor assembly includes a first face and a second face. The second face is on the opposite side of the sensor assembly relative to the first face. The sensor assembly also includes an electrical plug on the first face of the sensor assembly and an electrical outlet on the second face of the sensor assembly. The electrical outlet is of a same type that is complimentary to the electrical plug on the first face. The sensor assembly also includes a sensor for sensing a value of an environmental variable in a space and a sensor communication system for transmitting and receiving information.

Under a further aspect of the invention, the electrical outlet is controllable via the sensor communication system.

Under another aspect of the invention, the sensor assembly also includes a sensor processor system for deriving environmental characteristics of the space based on the value of the environmental variable in the space.

Under still a further aspect of the invention, the sensor assembly include at least one of a USB and other standard power outlet on the second face of the sensor assembly, in which the USB or other standard power outlet being controllable via the sensor communication system.

Under yet another aspect of the invention, the sensor of the sensor assembly includes at least one of a motion sensor, a humidity sensor, a temperature sensors, a pressure sensor, a CO Sensor, a CO2 Sensor, an acoustic sensor, an infrared sensor, an accelerometer, and a gyroscope.

Under an aspect of the invention, the sensor assembly is capable of acting as a network routing node.

Under another aspect of the invention, the sensor assembly also includes a plurality of sensors, each spaced apart from the other and a sensor processor system for determining a value for a gradient of an environmental variable based on information from the plurality of sensor.

Under an aspect of the invention, a sensor system includes a plurality of sensor assemblies disposed in a building. Each sensor assembly includes a temperature sensor for sensing the ambient temperature of the space within which the sensor is placed and a pressure sensor for sensing the ambient pressure of the space within which the sensor is placed. The sensor system also includes a sensor communication system for transmitting and receiving information and a sensor information aggregator that receives information about the ambient temperatures and ambient pressures sensed from the sensors of the plurality of sensor assemblies. The sensor information aggregator includes an aggregator communication system for transmitting and receiving information and an aggregator processor system for determining a temperature gradient in the building based on the information about the ambient temperatures and ambient pressures received by the sensor information aggregator.

Under a further aspect of the invention, at least one of the plurality of sensor assemblies is wall-mounted.

Under yet another aspect of the invention, at least one of the plurality of sensor assemblies is portable and carried by an individual.

Under still a further aspect of the invention, the aggregator processor system uses wireless communication signal strength between the sensor information aggregator and the sensor assemblies to estimate sensor assembly locations relative to each other. The determination of the temperature gradient is further based on the relative locations of the sensor assemblies.

Under an aspect of the invention, the aggregator processor system uses manually entered locations of sensor assembly locations relative to each other, and the determination of the temperature gradient is further based on the relative locations of the sensor assemblies.

Any of the aspects of the invention described above can be combined with any of the other aspects set forth herein.

BRIEF DESCRIPTION OF THE SEVERAL VIEWS OF THE DRAWINGS

For a more complete understanding of various embodiments of the present invention, reference is now made to the following descriptions taken in connection with the accompanying drawings in which.

DETAILED DESCRIPTION OF THE PREFERRED EMBODIMENTS

Figure 1:
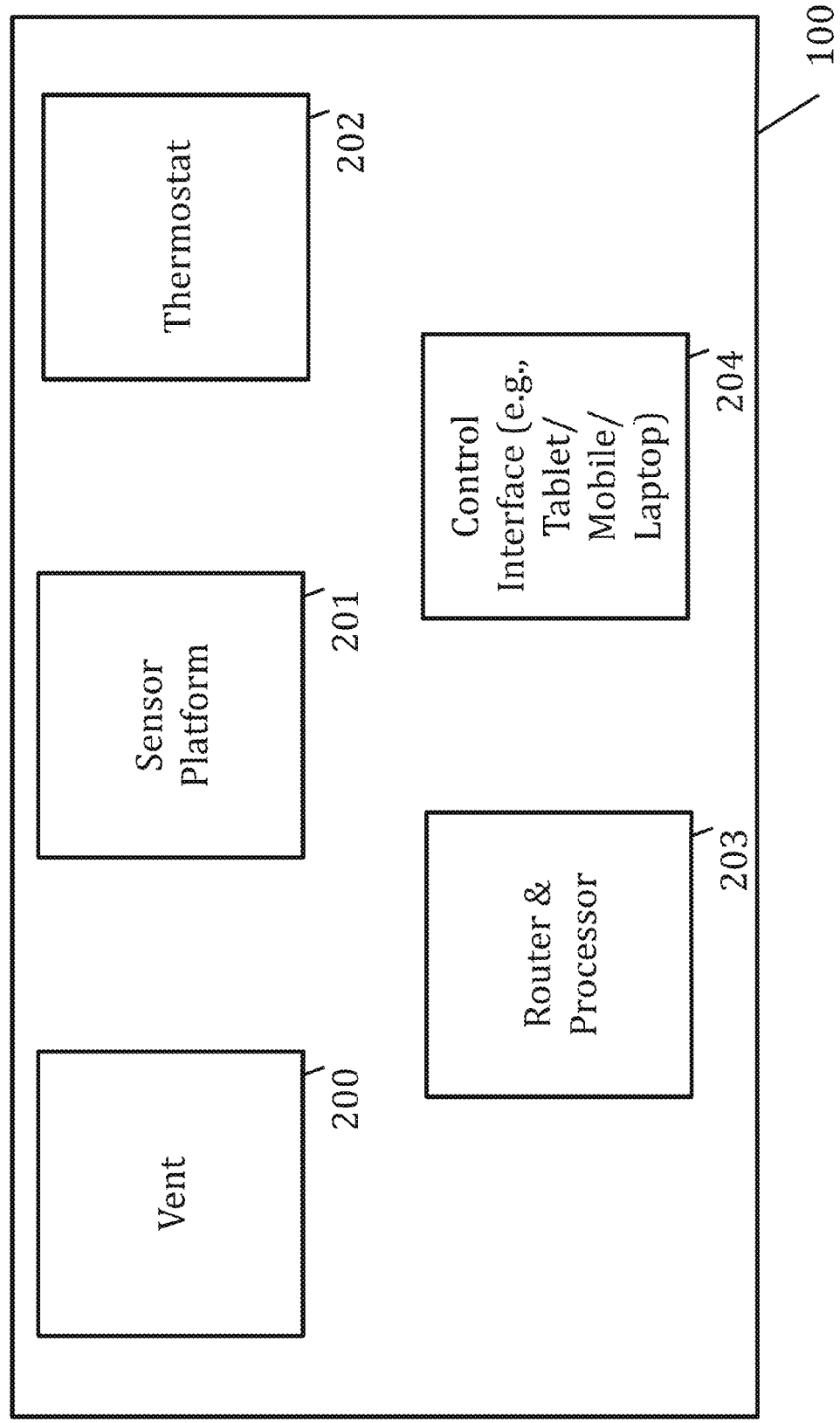
FIG. 1 illustrates an overview of a system for automatically adjusting airflow in a building according to an embodiment of the invention.

A system (100) described in this document is a novel approach to optimizing the airflow in a building (e.g., a home) based on user set goals for savings, comfort or both. In this implementation, the system is comprised of five major components as seen in FIG. 1. In one implementation there is a wireless Router & Processor that deploys a pre-configured wireless network (203) which communicates with the vents (200), Sensor Platforms (201), Thermostat(s) (202) and the Control Interface (204).

Figure 2:
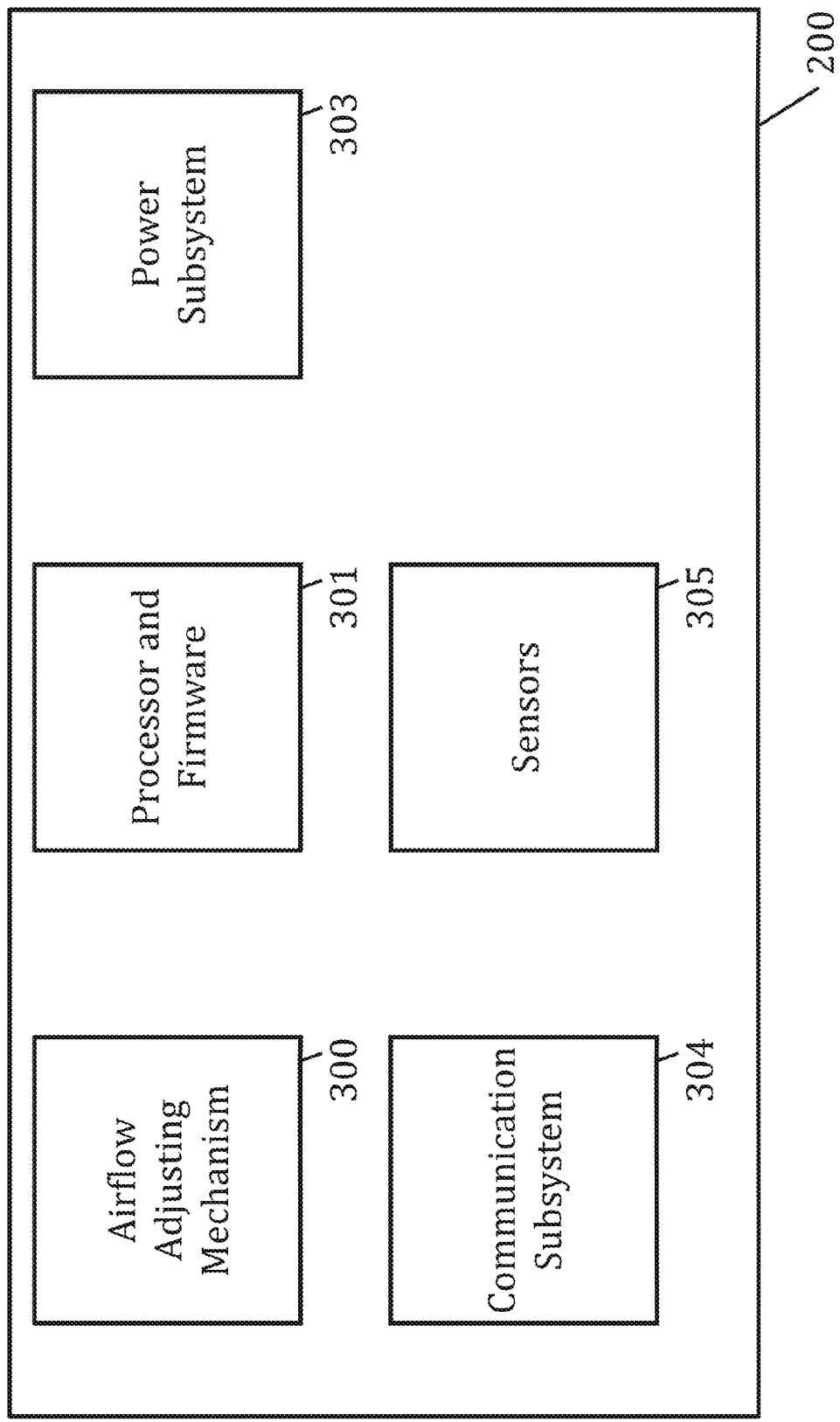
FIG. 2 illustrates an overview of a vent for automatically adjusting airflow to a space according to an embodiment of the invention.

In one implementation of the system, all of the vents in a home are replaced with new wirelessly controlled actuating vents (also called "vents" or controlled supply registers herein). In other words, the traditional covering (or faceplate) of the terminus of a portion of the duct work of a forced-air heating or cooling system is replaced. In an illustrative example, the terminus of the duct work is the location at which the duct stops flush with the wall or ceiling of a room. In another embodiment, only a few of these vents would need to be replaced. These vents allow the system to control the airflow within the existing ductwork, without damaging the HVAC system due to lack of airflow, within a home. Embodiments of such vents are shown in FIG. 2. In another embodiment no new vents are installed, but the system operates using impulses from the sensors alone. In this type of system, the HVAC is turned on/off based on temperatures in any room in the home—allowing much more control. For example, a user can instruct the system to maintain a bedroom at a desired setpoint. The system would cycle on and off to maintain the desired setpoint in the bedroom without regard for how the other rooms are affected. In another example, the system can be configured with more complex instructions, such as attempt to maintain a first room at a first setpoint but only if a second setpoint set for another room is not exceeded. In all cases the conditions inside of the ducts are measured and taken into account when controlling the vents. These are examples only, and other configurations are within the scope of the invention. In addition, while implementations of the invention are described as being used with HVAC systems, it is understood that systems that only heat, only cool, or only supply forced air are within the scope of the invention.

In one embodiment, the added vent closing device may be added into main return ducts. In another embodiment, an airflow control device may be added to a fresh air intake. With these additions the system can control outdoor air intake to improve energy efficiency, or meet occupancy fresh air demands if paired with $CO_2$ sensors. In one embodiment, this system may be operated as an HVAC economizer, or include operations that resemble an economizer. The system can thus add outdoor air when temperature or humidity conditions are favorable to driving the system temperatures in the right direction (heating or cooling, dehumidification or humidification). This will allow for "free" heating or cooling, as the system need not operate the heat pump, furnace, AC unit, or other cooling device to control the temperature, dramatically reducing energy consumption.

Figure 3:
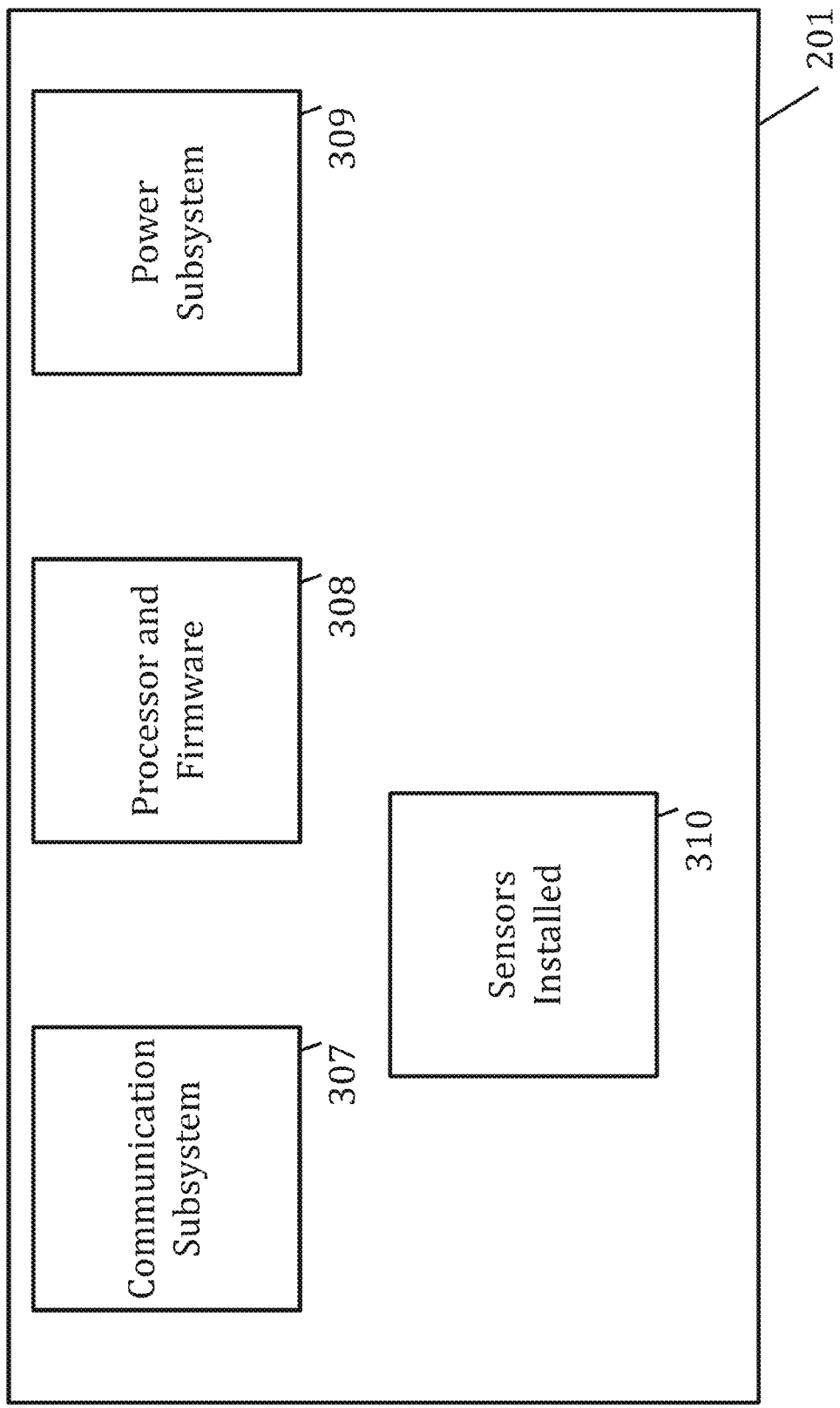
FIG. 3 illustrates an overview of a sensor platform for detecting a condition in a space according to an embodiment of the invention.

In one embodiment, the Sensor Platforms (201), as seen in FIG. 3, provide the Router & Processor (203) with real time data on the temperature, humidity, air pressure, and motion in the rooms within the home or building. The sensor platforms provide feedback to the Router & Processor which in turn controls the vents.

Embodiments of this system can vary in that the configuration of the vents (in quantity, integrated sensors, and opening and closing mechanisms), the sensor platforms (in both types of sensors installed (i.e. pressure sensors, multiple temperature sensors), as well as location and quantity), and the network protocol can change or adapt as long as there is a method for the system to receive feedback regarding the state of the home or building within which it is installed. This means, in various embodiments, only a few sensor platforms may be necessary if the system can determine the states of the whole home or building through correlation. In yet another embodiment, only one sensor may be installed, which is moved from room to room over a period of time, to develop an understanding of the home. In yet another embodiment, no sensors are deployed, and the system would gather feedback by querying the user.

In one embodiment, the system is added to a fixed volume air conditioning system. In another embodiment, the system is added to an existing variable air volume system for added control or to supplement problem areas. In another embodiment, the system is added to an active chilled beam system. In yet another embodiment, the system is added to a DOAS (dedicated outdoor air system). In other embodiments, the system may be added to other HVAC or other fluid providing systems.

Figure 6:
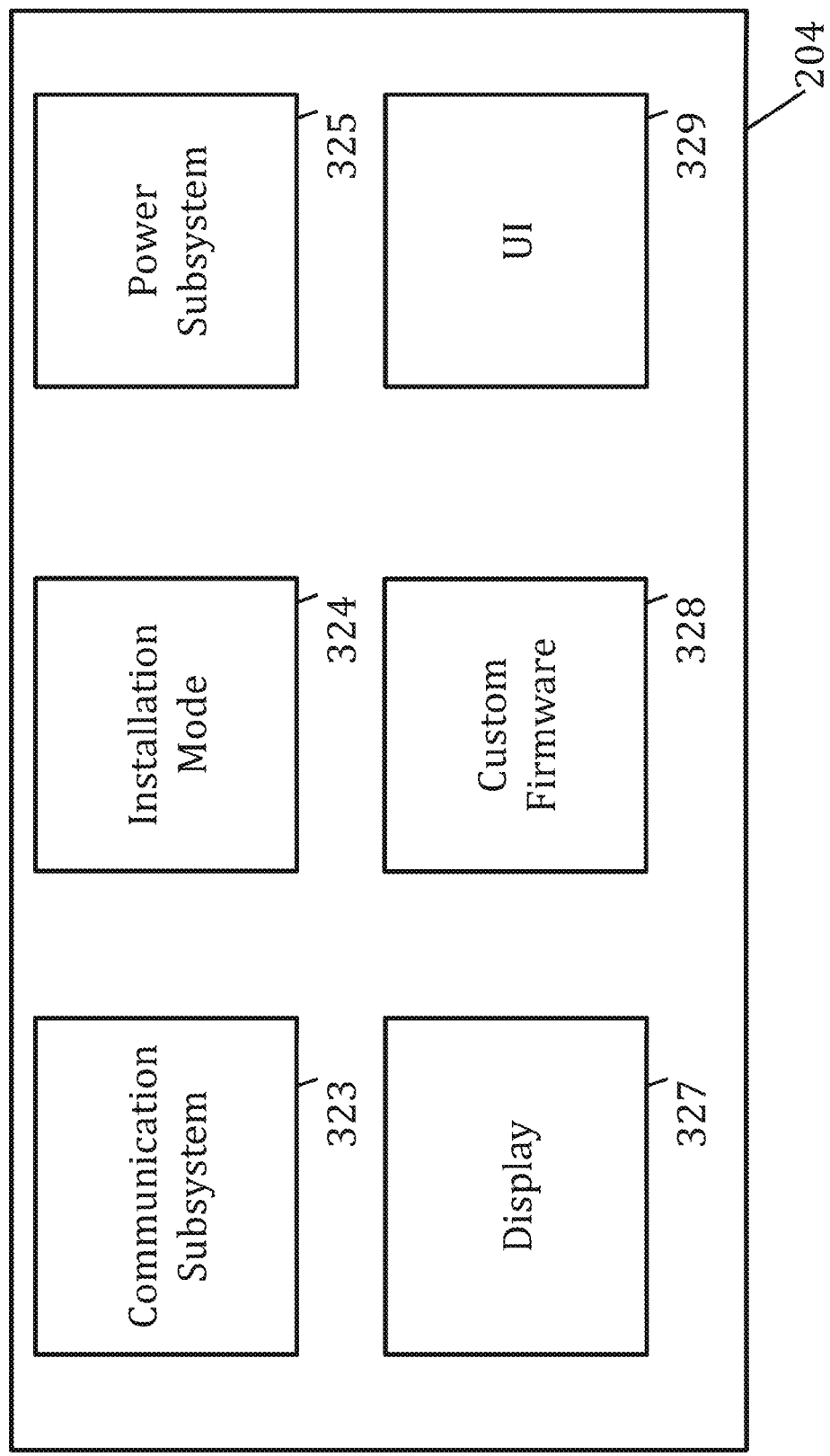
FIG. 6 illustrates an overview of a control interface according to an embodiment of the invention.

To control the system, in one embodiment the user uses the Control Interface (204), as seen in FIG. 6, to instruct the Router & Processor on the user's preferences for mode and/or temperatures for each room. Using the user's preferences (e.g., environmental variable set points), and feedback from the sensors, the Router & Processor adjusts the vents throughout the home in response to changing conditions to optimize the airflow and help the home reach equilibrium. More details and embodiments for the control interface are described later in this report.

In one embodiment, the system operates based on anticipated and/or current occupancy. The system may use occupancy-use patterns for each room or combinations of rooms to determine what hours of the day and days of the week to operate. In one embodiment, the system uses occupancy sensors, which may include infrared, acoustic (passive or active ultrasonic sensors), microwave detector sensors, or other sensors. In another embodiment, the system may detect a device on a person, such as a smartphone, tablet, laptop, or other wifi/Bluetooth/electromagnetic wave emitting device to detect occupancy. In one embodiment, the system may interface with existing or new lighting systems that employ occupancy sensors, using the same sensors for both. In controlling the zones and adapting, the system may employ adaptive control, neural networks, fuzzy logic, thermodynamic modeling of HVAC zones, fan power energy consumption modeling, minimum outdoor air, room use type, predictive heating demand control, dynamic occupancy patterns, or other control methods. In another embodiment, the system operates based on fixed schedule. In yet another, the system operates using preferences set by the user. In yet another, the system allows individual zoning of each room, allowing the user to set the conditions of each room independently.

In one embodiment, the system uses pressure as an input. In another embodiment, the vents use pressure and temperature as inputs. By measuring the pressure within the ducts, or calculating it based on other measurements, the system can prevent creating a pressure environment that impacts the health of the existing HVAC system, or efficiency. By using both pressure and temperature a better estimate of system health is obtained. In one embodiment, the vent (as shown in FIG. 2) has pressure sensors on the device. In another, pressure sensors are placed within or affixed to the duct and communicate to the system. In one embodiment, pressure may be measured on the sensor platform (as seen in FIG. 3), then calculations can be applied to understand the pressure on the system. In another, the pressure measurement is used to calculate volumetric airflow through the vent. In another embodiment pressure is measured on each sensor platform. By using pressure and temperature measurements at all, or even a subset of, sensors and vent locations the local temperature gradient can be deduced. This calculation allows comfort at any height in the building to be calculated and better controlled. When determining a temperature or any other gradient for an environmental variable, the information about the environmental variables can be collected by a sensor information aggregator. The aggregator can use manual locations for the sensors provided by the user or the system can determine the positions of the sensors relative to each other using wireless communication signal strength between the sensors and the location of the aggregator. The aggregator can reside in any of the components of the system described herein, and it performed the determination of the gradient value based on the information supplied by the various sensors.

In one embodiment the Router & Processor (FIG. 5) controls the existing HVAC unit within the home through the thermostat (202), which receives wireless instruction from the processor and thus actuates the HVAC system. In yet another, the system may instruct the user to turn on and off their system. In yet another, the router and processor may communicate directly to the HVAC unit through a wireless interface built into the HVAC, or added on. The concept here is that the Router & Processor, using feedback from the sensor platforms, vents, and a smart learning control algorithm that optimizes the use of the HVAC system for any situation. The algorithm uses machine learning techniques in combination with data collected from the vents, sensors, and user inputs to learn the characteristics of the home including heat loads, air leakage, humidity load, forced air pressure characteristics, and others. Once the algorithm learns the characteristics of the home, the use of the HVAC system can be optimized according to a blend of comfort and economy according to user preferences. The user can also be alerted to sudden changes in system characteristics that may indicate an anomaly that warrants attention. In one embodiment the algorithm learns the home characteristics through normal use. In another the algorithm exercises the entire home HVAC and system components in order to learn more quickly and completely the home characteristics.

The Vent, as shown in FIG. 2, includes an Airflow Adjusting Mechanism (300), a processor with firmware (301), a power subsystem (303), a communication subsystem (304), and sensors (305). In one embodiment, the vent receives wireless instructions from the Router & Processor (203) via the communication subsystem (304). In another, the vent may receive wireless instructions directly from the sensor platforms. In another, the vent may receive wireless instructions directly from the Control Interface.

The Vents in the system are the component of the system that impacts airflow within the house in a real time fashion. The vents open and close using an airflow adjusting mechanism (300) that control the amount of air allowed through the vent when the system is running. The sensors on the Vent can optionally include an air flow measurement device.

Figure 13:
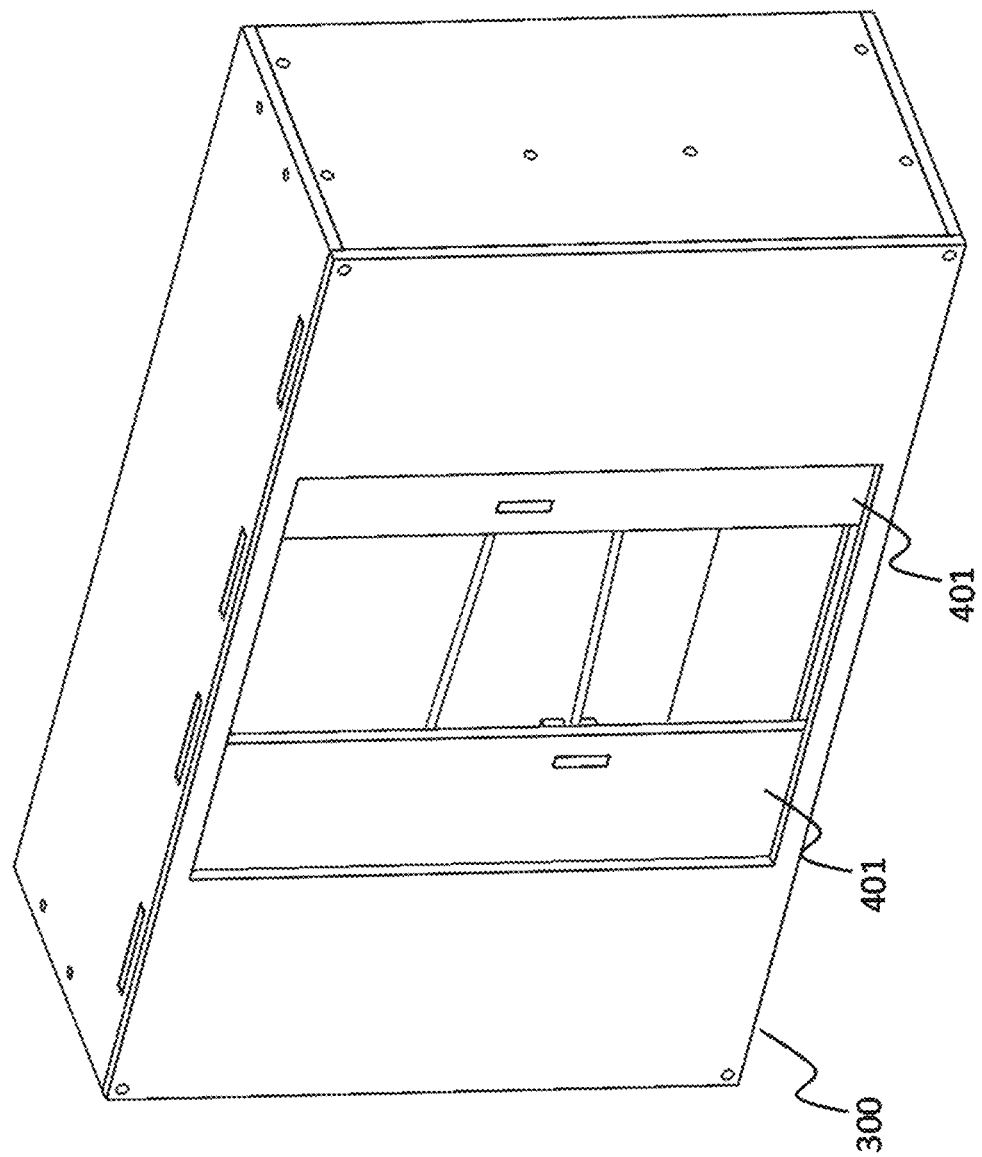
FIG. 13 illustrates an exterior perspective view of a vent according to an embodiment of the invention.
Figure 14:
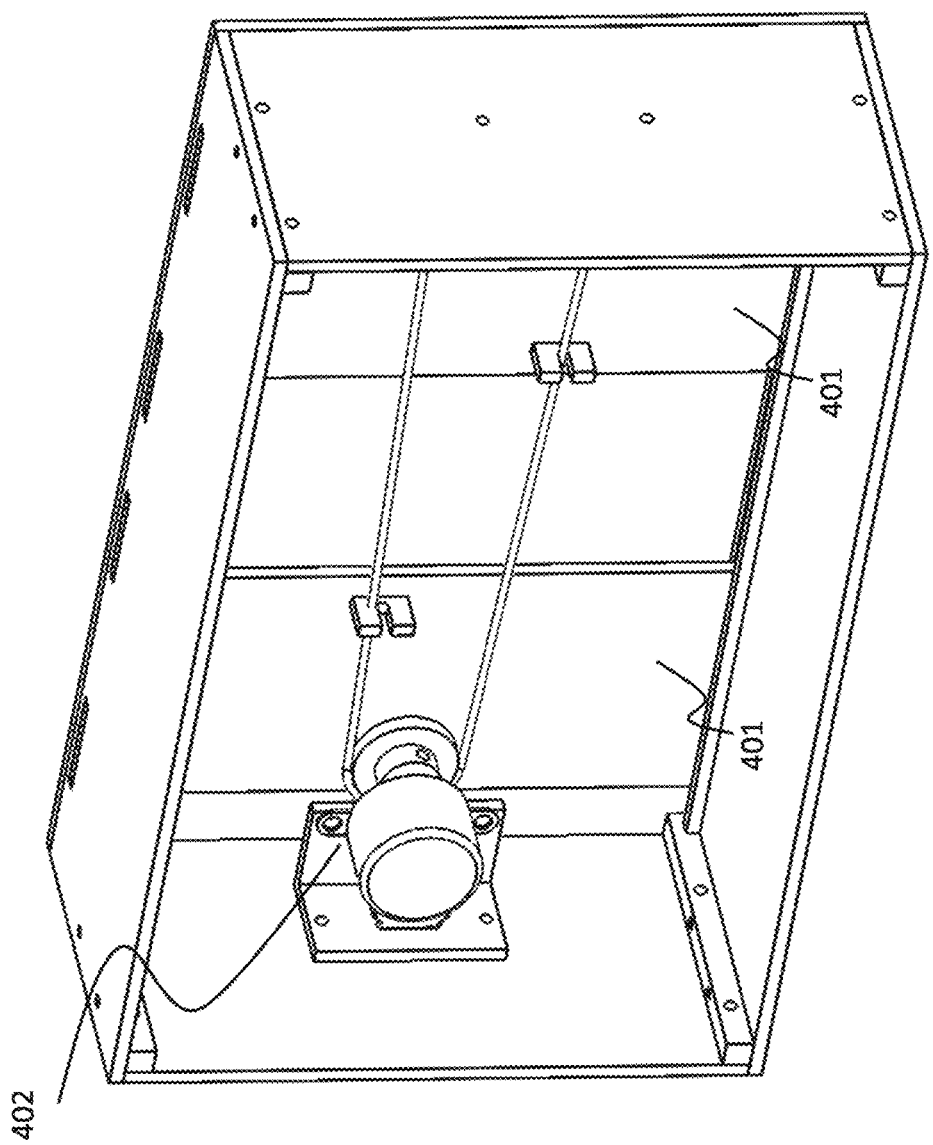
FIG. 14 illustrates an interior perspective view of a vent according to an embodiment of the invention.

There are a few components in certain embodiments of the vent (pictured in FIGS. 13,14). The first being the airflow adjusting mechanism themselves (300). This airflow adjusting mechanism is comprised of a mechanism that constricts the air (401), and a mechanism to control the constrictor (402). In regards to the constricting mechanism (401), these are the devices that constrict the air. They are controlled by a movement mechanism that serves to adjust the constriction level. The movement mechanism (402) operates the constricting mechanism in response to an instruction received from an outside controller, such as the processor and firmware (301).

In regards to the air constricting mechanism (401), in one embodiment, the louvers are horizontally mounted. In another, they are vertically mounted. Yet in another embodiment, these louvers are a shutter mechanism, similar to that of a curtain that is mounted horizontally or vertically. Yet in another embodiment, the mechanism is an iris, similar to that of a camera aperture. Yet in another embodiment, this mechanism is a parachute configuration, where a semi rigid membrane is extended to catch the air. A novel concept here is to constrict the air in a manner best suited for the needs of the system. This includes balancing reliability with cost, motion with battery life, and constricting the air in a manner to minimize audible noise and other undesired side effects. Moreover, adjustments in airflow can take into account future weather forecasts when determining what is needed to maintain a user's desired environmental variable set point. In one embodiment, the air constricting mechanism replaces the existing exterior duct grill. In another embodiment, the air constricting mechanisms is mounted in the interior of the duct. Interior mounting may use springs with significant normal force, screws, adhesives, or other methods.

In one embodiment, adjustable size louvers will be added to fit different duct sizes, for either interior or exterior grills. In one embodiment, duct louvers telescope, to adjust to larger sizes. Space between louvers may vary as well, with hinges, springs, or other methods to adjust the spacing. In one embodiment, the system employs a fabric which constricts to block flow. In another embodiment, the system may include multiple arms or springs to allow for installing at a slanted angle relative to the duct, allowing for application to multiple different heights.

In regards to the mechanism that controls the constrictors (402), in one embodiment, a motor is used. In another, a stepper motor is used. In yet another, a solenoid is used. In yet another embodiment, memory wire, or metal that changes shape due to an electrical impulse is used. In yet another embodiment, electromagnets are used. In another embodiment, a material that changes shape at different temperatures due to thermal expansion is used. In even another embodiment, the air coming from the duct is used to adjust the constrictors.

The Airflow adjusting mechanism (300), as seen in FIGS. 2 and 13, is controlled using custom firmware loaded on a processor (301). This firmware has algorithms to accept commands from the main Router and Processor (203) or other outside controller to control the vent itself. It has algorithms to open and close vents, send sensor information and state information back to the router and processor, and intelligence to minimize power use of the vent itself. It also has algorithms to process the information from the onboard sensors on the vent (305).

The processor and firmware receives instructions from the router and processor (203) via the communication subsystems (304). The communication sub system receives signals wirelessly through Wi-Fi (802.11). In other embodiments, the system receives signals via an analog RF signal, ZigBee, 802.15, Z-Wave, Bluetooth, infrared, other types of electromagnetic waves, or another wireless method. In another embodiment, the system communicates via electrical wires, a wired configuration. In other embodiments, the system and subsystems may communicate in any combination of the above methods.

It is noted that in one embodiment, the communication subsystem (304) and the Processor and Firmware (301) are integrated into a single device.

Figure 5:
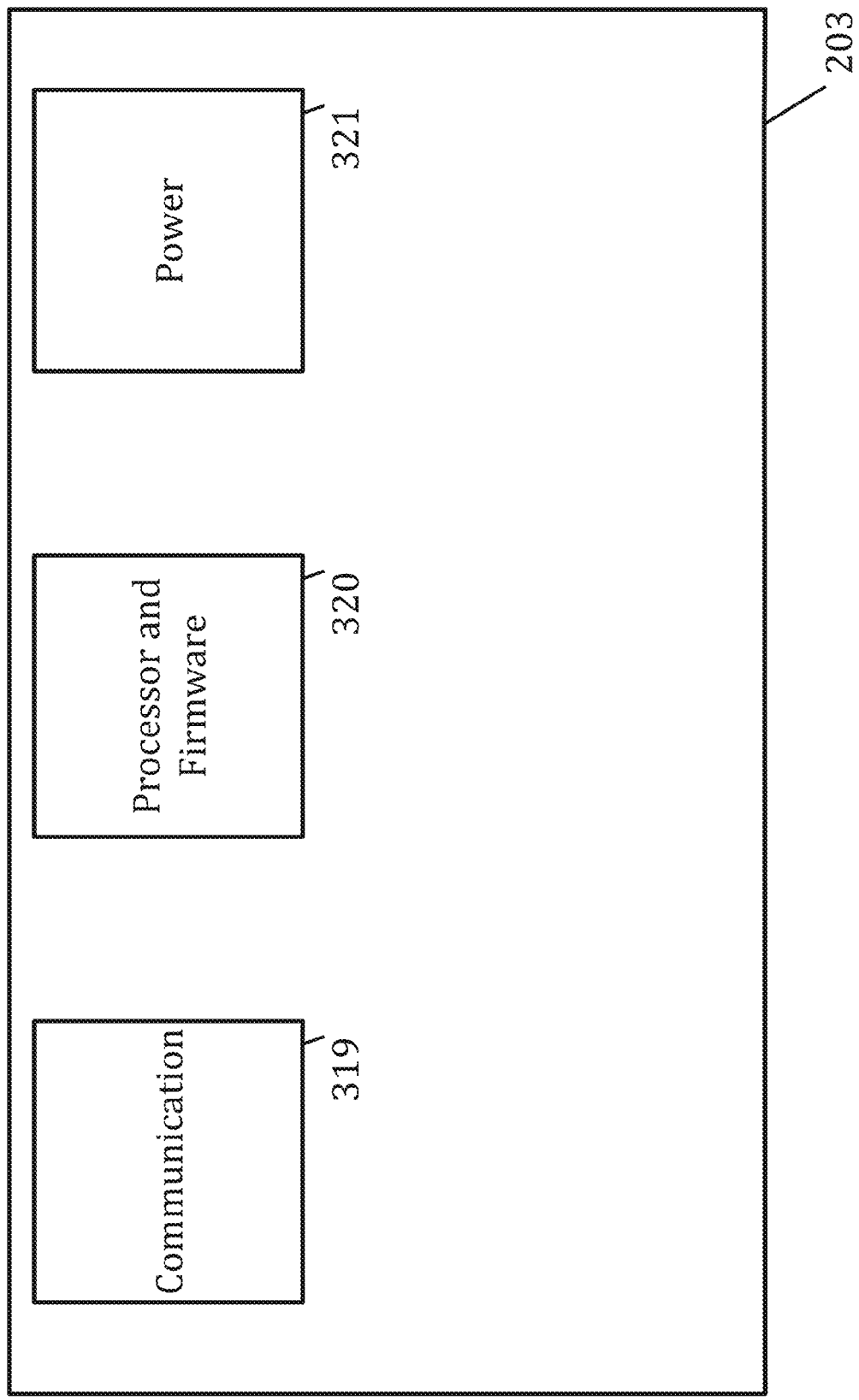
FIG. 5 illustrates an overview of a router and processor according to an embodiment of the invention.

In one embodiment the vent includes sensors (305) such as pressure and temperature sensors (408), as shown in FIG. 5, on the vent to monitor real time pressure in all ducts to avoid placing the HVAC system in a stressful or damaging environment. In other embodiments, other sensors are included, such as sound, air speed, temperature, humidity, $CO_2$ levels, occupancy, and other sensors as well. In yet another embodiment, sensors may be removed entirely. In one embodiment, the sensors on the vent's primary purpose is to understand the airflow characteristics (such as velocity, pressure, temperature, humidity) being presented to the HVAC system for the purpose of preventing damage to the system while modifying those airflow characteristics.

Figure 15:
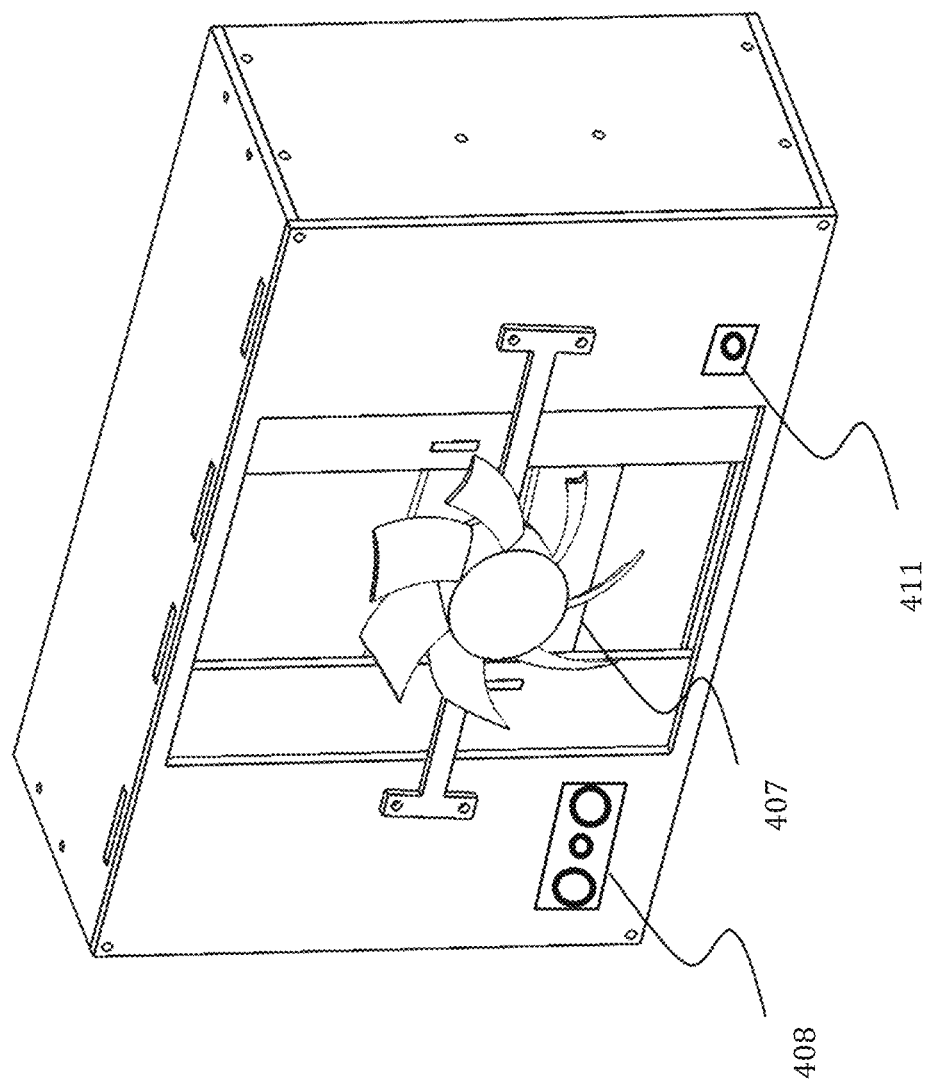
FIG. 15 illustrates an exterior perspective view of a vent according to an embodiment of the invention.
Figure 16:
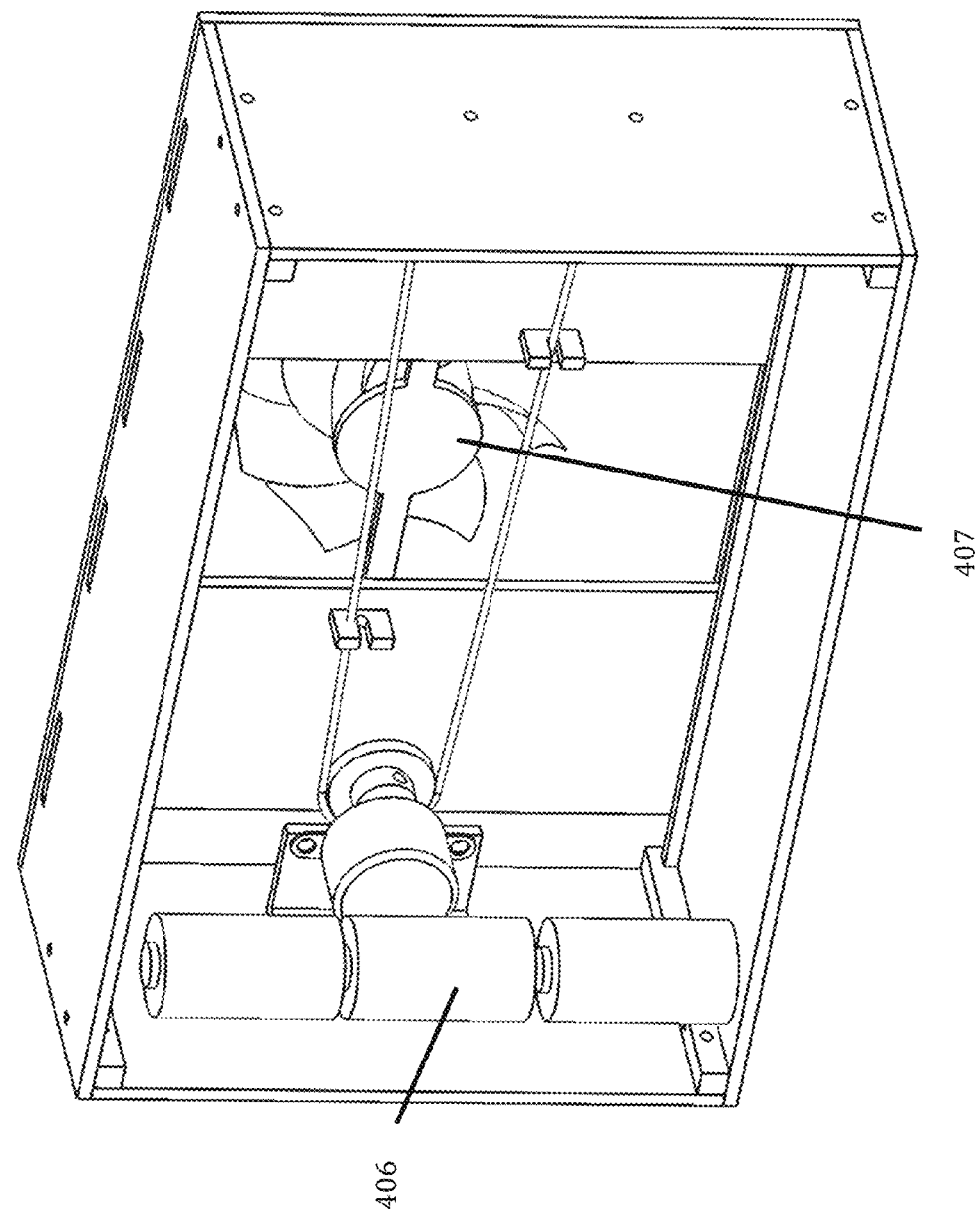
FIG. 16 illustrates an interior perspective view of a vent according to an embodiment of the invention.

In one embodiment, the vent is wireless. As such, they include a power source on the vent itself. The power subsystem (303), in one embodiment includes a battery (406). To maximize battery life, the vent may also include power generation (407) on board as shown in FIGS. 15 and 16, for use with a rechargeable battery. This power is generated using the air within the vent itself through a turbine. In another embodiment, the power is generated using vibration within the vent. In yet another embodiment, power is generated using solar panels. In another embodiment power is generated via a thermo-electric device such as a Peltier generator. In another embodiment, power is provided by a capacitor. In another embodiment, a means of mechanical energy storage such as a spring may be used. In yet another embodiment, a piezoelectric device may be used, which may capture vibrations or be paired with a part moved by the airflow. This part may use a flexible horizontal plate that oscillates in the airflow, an unstable small "wing" that uses lift to oscillate, or other devices. In yet another embodiment, power is provided to the vents via a power source such as a local outlet, or the central breaker.

In one embodiment the system includes active noise cancellation technology (411) on the vents. In this embodiment the vents reduce noise levels due to airflow and ducting by actively cancelling the noise before it exits the vent. In such an implementation, a noise cancellation module samples the noise arriving at the vent from within the ducting with one or more microphones, determines the appropriate sound waveform to reduce the noise level, and produces the waveform using one or more speakers within the vent.

In one implementation, vents may use seals or gaskets on the outside to ensure a tighter seal once the vent is installed to maximize efficiency and comfort. In another, vents may clamp against the duct to ensure a tight seal. In another embodiment, duct insulation may act as a barrier to air leakage.

In another embodiment, the system acts to encourage airflow instead of restricting it, employing a fan or other device to provide additional driving force for the air.

Figure 17:
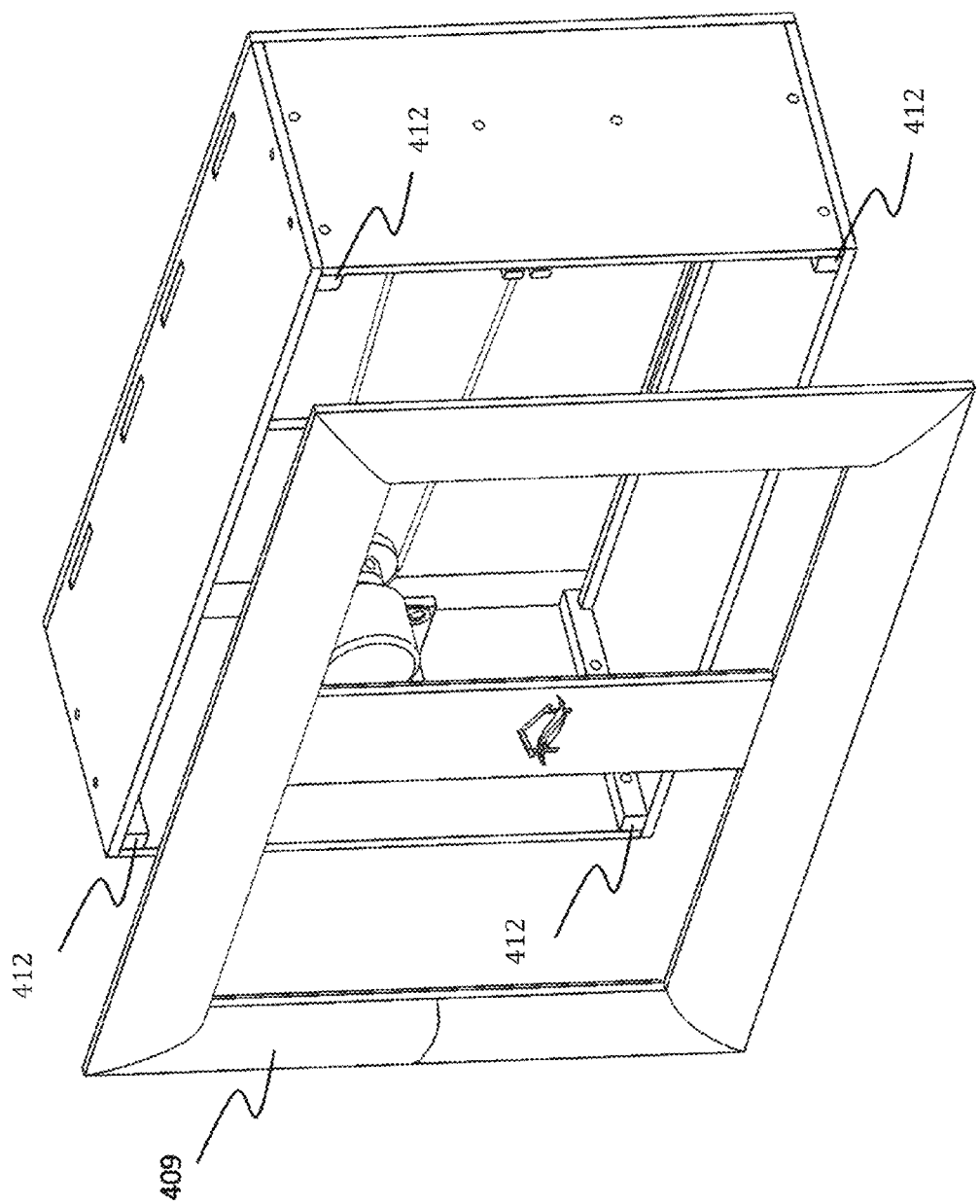
FIG. 17 illustrates an exterior perspective view of a vent with a faceplate according to an embodiment of the invention.

FIG. 17 presents a front plate (409) that can be installed and removed without tools. In one embodiment, the plate is attached with magnets (412). In another, a hook and loop attachment is used; further still, a slide mechanism is used in another.

Figure 18:
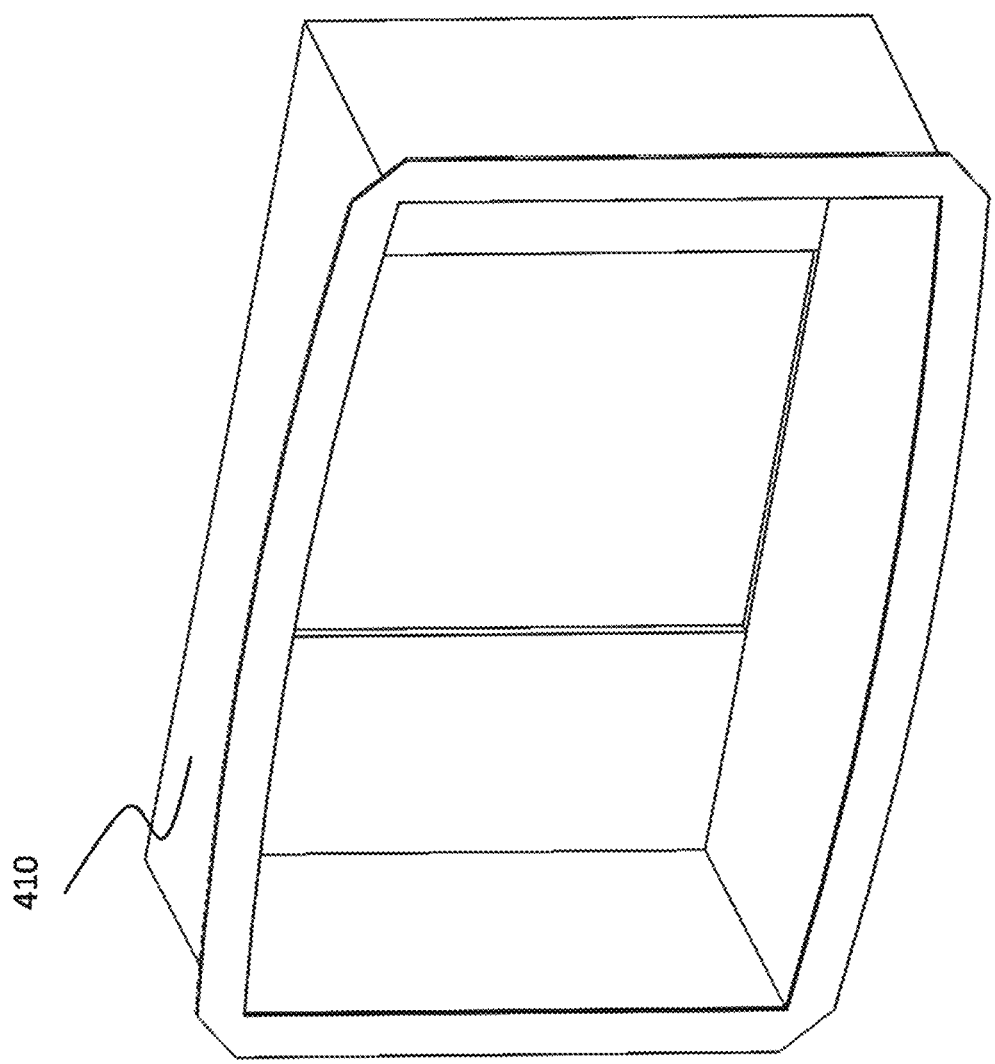
FIG. 18 illustrates a perspective view of a vent fitting according to an embodiment of the invention.
Figure 19:
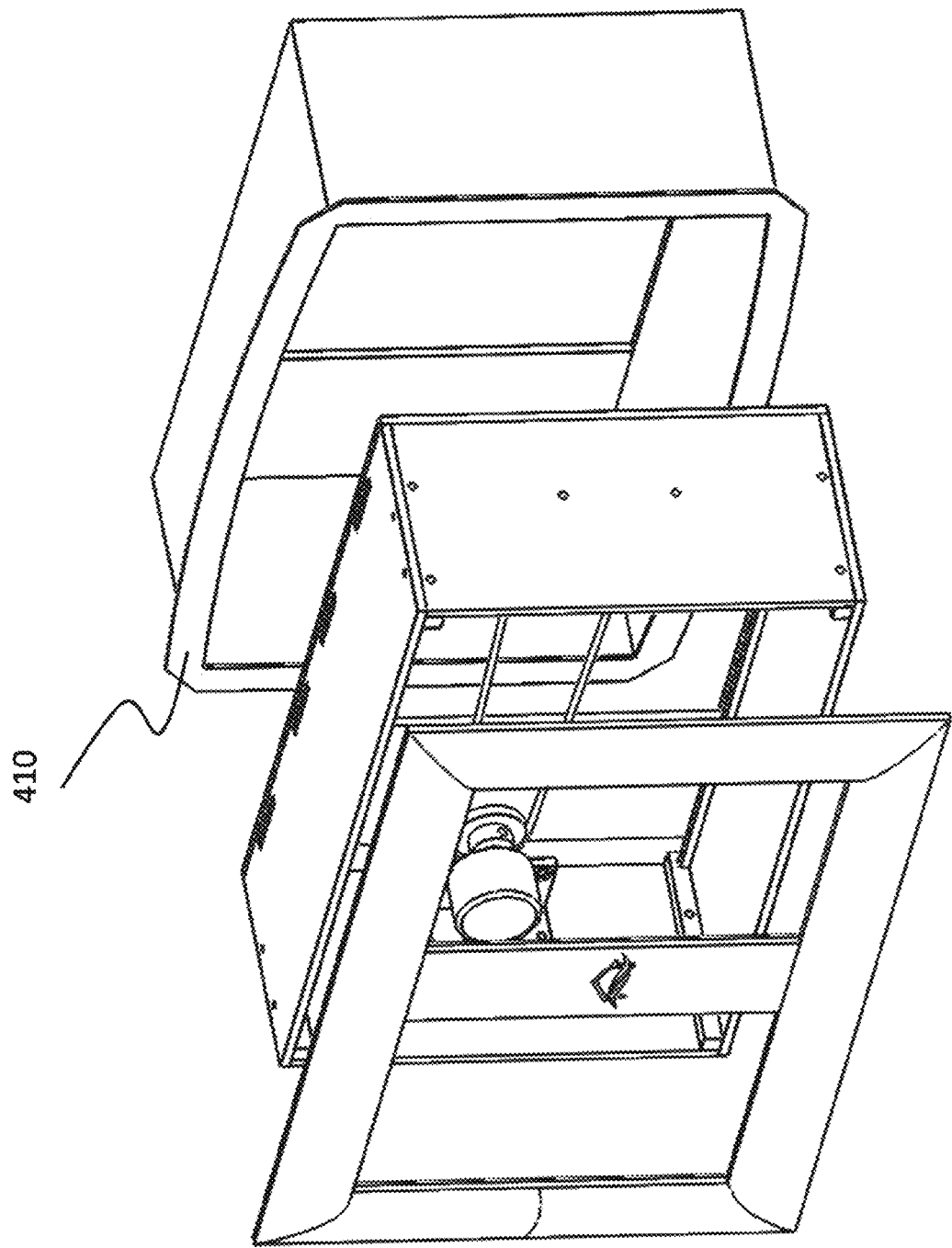
FIG. 19 illustrates an exploded perspective view of a faceplate, vent, and vent fitting according to an embodiment of the invention.

In one embodiment the vent installs in the home without the use of tools. In one embodiment this is accomplished by a warped shape (410) in the vent that creates a friction fit as shown in FIGS. 18 and 19. Specifically, the top and bottom of shape (410) are bowed slightly outward. In another a lever mechanism engages the wall. In another wedges may be inserted by hand between the vent and the duct.

The faceplates of the vents are designed to diffuse air in a more efficient and quieter manner. These faceplates provide the same amount of diffusion, while presenting a lower pressure load on the existing HVAC system—meaning the vents themselves are more efficient than existing solutions. By lowering the "all open" pressure, the vent allows more potential to add pressure to the system without reaching a damaging state. In other words, such vents have a greater range of back-pressure available.

In one embodiment of the system, the sensor platform (201) is employed to provide feedback to the Router & Processor.

In one implementation, the sensor platform, as seen in FIG. 3, uses temperature, motion, and humidity sensors (310) to detect characteristics of the environment and send that information through the Processor and Firmware (308) via the communication subsystem (307). In another implementation, the sensor platform senses ambient pressure. In this embodiment the sensors correlate pressure altitude with temperature to form a temperature gradient. In another, the sensor platform has two temperature sensors, allowing the system to calculate temperature gradients. In another embodiment the sensor platform has sensors mirrored on the top and bottom so that accurate measurements are taken despite the orientation of the outlet that the sensor is plugged into.

In another implementation, the sensor platform may also sense Carbon Monoxide, VOCs, Carbon Dioxide, humidity, or air quality. In yet another, they may only sense temperature. In yet another, they may include audio sensors, motion sensors, infrared sensors, an accelerometer, or a gyroscope (solid state or otherwise). In yet another, they may include video or other optical sensors. In several embodiments, the motion, Carbon Monoxide, Carbon Dioxide, acoustic, optical, or other sensors may be designed to detect occupancy. Thus, detection and manipulation/control of any of the aforementioned environmental variables is within the scope of the invention.

In one embodiment, the communication subsystem may also act as a WiFi repeater to increase WiFi coverage, or a repeater for any other wireless protocol employed as part of the main communication system used in the system. In another embodiment, the sensor suite may deploy a WiFi network and act as a hub for the system. In certain embodiments, it is preferred that particular sensors be wall-mounted, and, thus, stationary, while other sensors be portable.

Figure 20:
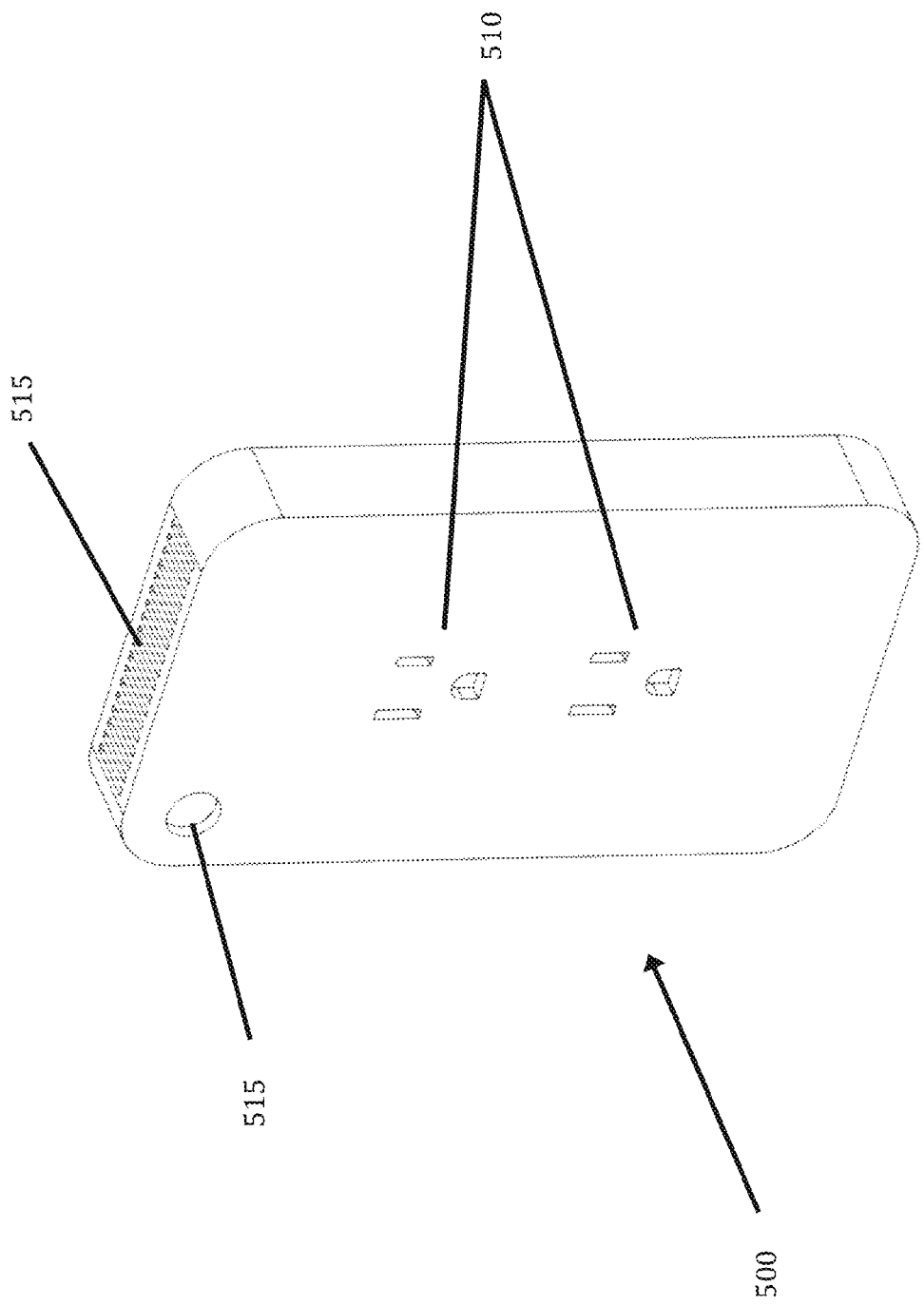
FIG. 20 illustrates a front perspective view of a pass-through sensor according to an embodiment of the invention.
Figure 21:
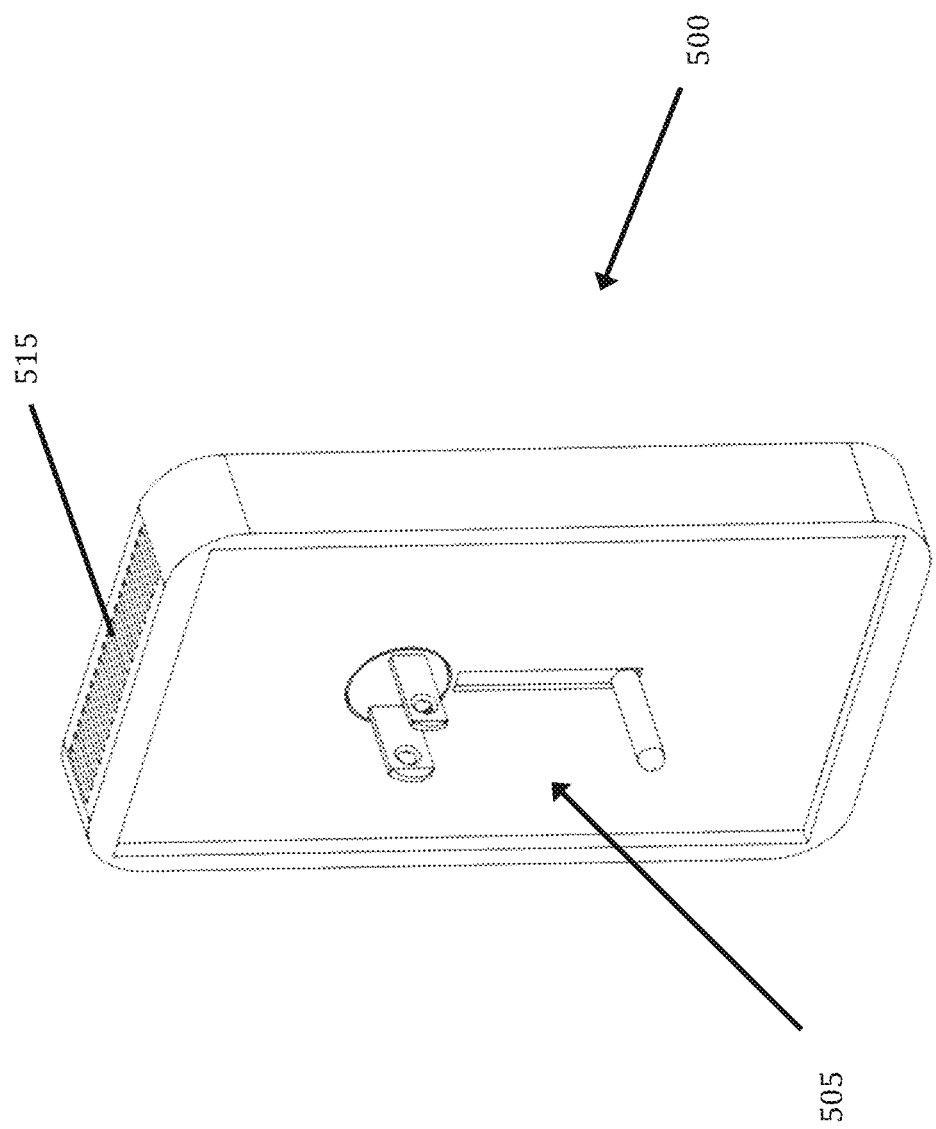
FIG. 21 illustrates a rear perspective view of a pass-through sensor according to an embodiment of the invention.

FIGS. 20 and 21 show one implementation (500) of the sensor platform (201). Sensor device (500) derives its power from a wall outlet using a standard plug (505). In another implementation, a sensor platform include batteries. In yet another, they may be light-powered. The Power Subsystem (309) ensures that regardless of the source of power, the sensor platform itself receives clean power so as not to compromise the accuracy and precision of the sensors installed.

In one embodiment, the power subsystem (309) may also supply a number of USB Ports to allow the user to charge devices.

In one implementation the sensor platform (309), as shown in sensor device (500), includes pass-through plugs (510) so that when the user installs them, they do not lose an outlet within their home. Optionally, sensor device (500) has openings (515) that provide access to sensors within the device.

In another implementation the sensor platform may provide wireless control of the pass through plugs individually.

In another implementation the sensor platform may have modules to expand it's capability that are attachable via an exposed port such as USB (not shown).

As mentioned above, the communication system is Wi-Fi (802.11), however in other embodiments can include Zig-Bee, 802.15, Z-Wave, Analog RF, Bluetooth or infrared or hard wired communication.

The next component is the Router and Processor, as seen in FIG. 5.

In one embodiment, we can install our own router and processor (203). This device is a router that deploys a wireless network. It may also connect to the internet with the communication system. This device may include our code already integrated, or packaged with a small computer or microprocessor that houses our firmware.

In another embodiment the sensors use their onboard capabilities to provide the routing and processing capability. In this embodiment a single sensor may act as the router and processor or the tasks may be distributed automatically and dynamically amongst the installed sensors.

In another embodiment, code is integrated on an existing wireless network by integrating it into existing compatible routers, and use that to integrate our devices. In all embodiments, any of the protocols mentioned earlier may be deployed.

In one embodiment, the processor and firmware (320) for the router and processor (203) houses the algorithm and control system, communication capabilities (319), and a power supply (321). The algorithm, and control system offers multiple modes. One mode is the installation mode, which enables the user to install the system. Another mode is the operation mode, where the algorithm receives stimuli from all the sensors platforms installed (201), the vents (200), the thermostat (202) and the control interface (204) to optimize operation in the home. The installation mode is described later in this document. The operation mode algorithm flowchart is presented in FIG. 7.

This operation mode algorithm may take into account all the variables mentioned earlier, such as humidity in each room, temperature in each room, motion in each room, vent state in each room, as well as other variables including but not limited to: location of sun, local outdoor weather, number of windows in the room, location of the room, and cloud cover among others. This algorithm may also take into account user preferences, which include but are not limited to: comfort zones, priority, schedule, and location. The algorithm is complex enough to learn and has variables necessary for successful home or building optimization, and future growth, but simple enough to implement and execute.

Figure 4:
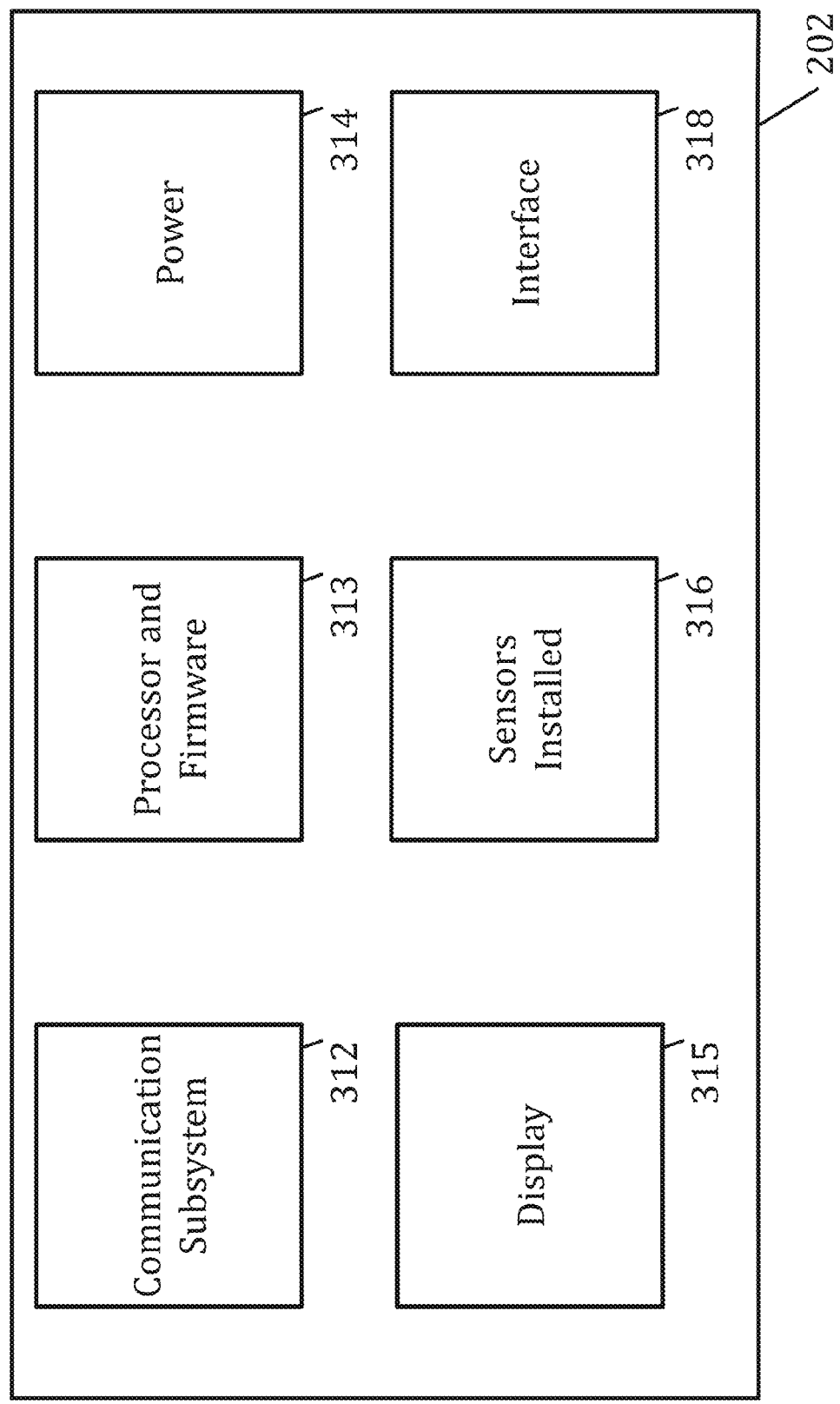
FIG. 4 illustrates an overview of a thermostat according to an embodiment of the invention.

The next component in the system is the thermostat as seen in FIG. 4.

In one embodiment the thermostat can be mounted on a wall and includes a power system (314) to provide power, processor and firmware (313) to process data and instructions given via the Communication (312) or the interface (318). In one embodiment there is a display (315) used for status and message reporting. The thermostat is used to control the HVAC system in response to stimuli received from the main router and processor (203) via the operation mode algorithm. Optionally, the thermostat (202) may include one or more on-board sensors (316), as described in connection with the sensor platform (201).

In one embodiment, the Thermostat features an e-paper or similar display to minimize power draw. The thermostat on the wall can also be controlled via the control interface (204) rather than the Router and Processor (203).

In yet another embodiment, the thermostat may be another device which includes an API (Application Programming Interface) to allow remote control of the device by our system.

In yet another embodiment, the user may not replace the thermostat but prefer manual control as given direction by the system through the control interface.

In yet another embodiment the system may not interact with the existing thermostat and only respond to predicted performance of that thermostat.

The final component is the control interface (204), shown in FIG. 6. In one embodiment, the control interface includes a communication subsystem (323), a power subsystem (325), a display (327), custom firmware or software (328) and a user interface (UI)(329). Optionally, instructions to support an installation mode (324) can be included or can be part of the custom firmware (328).

In one embodiment the control interface is a 10" (or equivalent) Android tablet, with a custom application loaded on with a custom android rom. In another embodiment, the user may use their own device running a custom native or web based application.

The device has multiple functions. The first is the installation mode (FIG. 8) as described in the following sections, enables a novel method of using the control interface as a feedback device to instruct a user through system installation.

Figure 7:
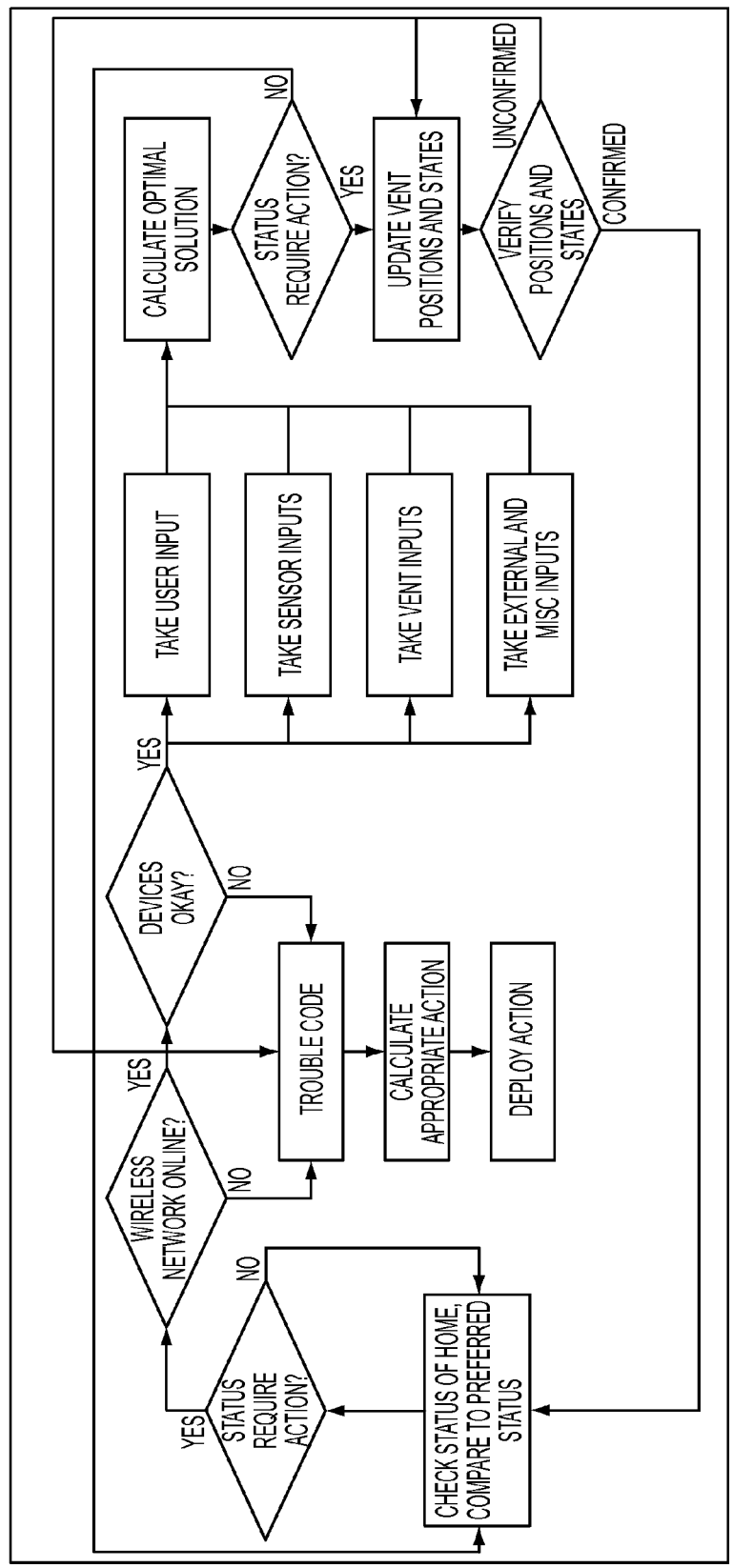
FIG. 7 illustrates an operational mode routine according to an embodiment of the invention.

Another function is to configure the control interface to allow the user to control the system, denoted Operation Mode (Algorithm Flow presented in FIG. 7). The UI (329) of the Control Interface produces multiple screens to allow control of the system using custom firmware. The device communicates with the Router & Processor through the communication sub system, (323) which uses WiFi or one of the other embodiments mentioned above.

In one embodiment the control interface allows the user to see all the zones in their home, multiple statuses (such as motion, temp and humidity) and set schedules and priorities for the system. In one embodiment, the system allows the user to set modes for the home, and see status from all the components the system controls.

In another embodiment, the user may select an automated zone where the system calculates everything by querying the user on comfort.

In another embodiment, the system operates and calculates the ideal state based on occupancy. In another embodiment, the user may use the tablet device to set occupancy manually. When determining what adjustments are needed to attain the desired conditions in the one or more rooms or spaces in a building, the system can send airflow values to be maintained by the one or more vents in the building or can provide relative feedback, e.g., that one or more vents needs to open more or close more relative to its present setting.

In yet another embodiment, the system may be configured to pick the best configuration to save the most energy.

In one embodiment, this interface also provides status to the user regarding the battery life of devices, communications status, and the overall health of not only the system, but the systems it controls (i.e. update the user on potential faults within their existing HVAC system).

In one embodiment, the supplied tablet device is open for use by the user as a conventional Android tablet.

In the Installation Mode (FIG. 8), the supplied control interface is used as a feedback system for installing the rest of the system. While this embodiment focuses solely on how aspects of the system are used in setting up the system itself, the same principles are applied to many different applications, such as installing appliances, TV's, computers and computer equipment, sound systems, even self-assembled furniture. For instance, imagine the installation of a new TV. When performing the install of the TV, an application on the phone would be employed to aid installation. When you plug the TV in, it finds the devices (through a wireless protocol such as WiFi), then provides instructions on how to install it. For instance, if you want to install a cable box, it walks you through which cables to install, and what to press on the remote. Essentially because the TV can communicate with the installation App, it can walk you through the installation step by step.

The embodiment presented in FIG. 1 describes the architecture necessary for using the Control Interface as an installation device. In this embodiment, the control interface receives stimuli from the Router & Processor—which is the key installation feedback stimuli. In future embodiments, the vents and sensor platforms are substituted. In other embodiments, no other devices may be used, by simply using the camera or other sensors on the Control Interface, the system can surmise correct installation steps as defined by user manuals.

FIGS. 8-12 present flow charts for the installation mode as it applies in this embodiment, for installing a specific embodiment of this system.

Figure 8:
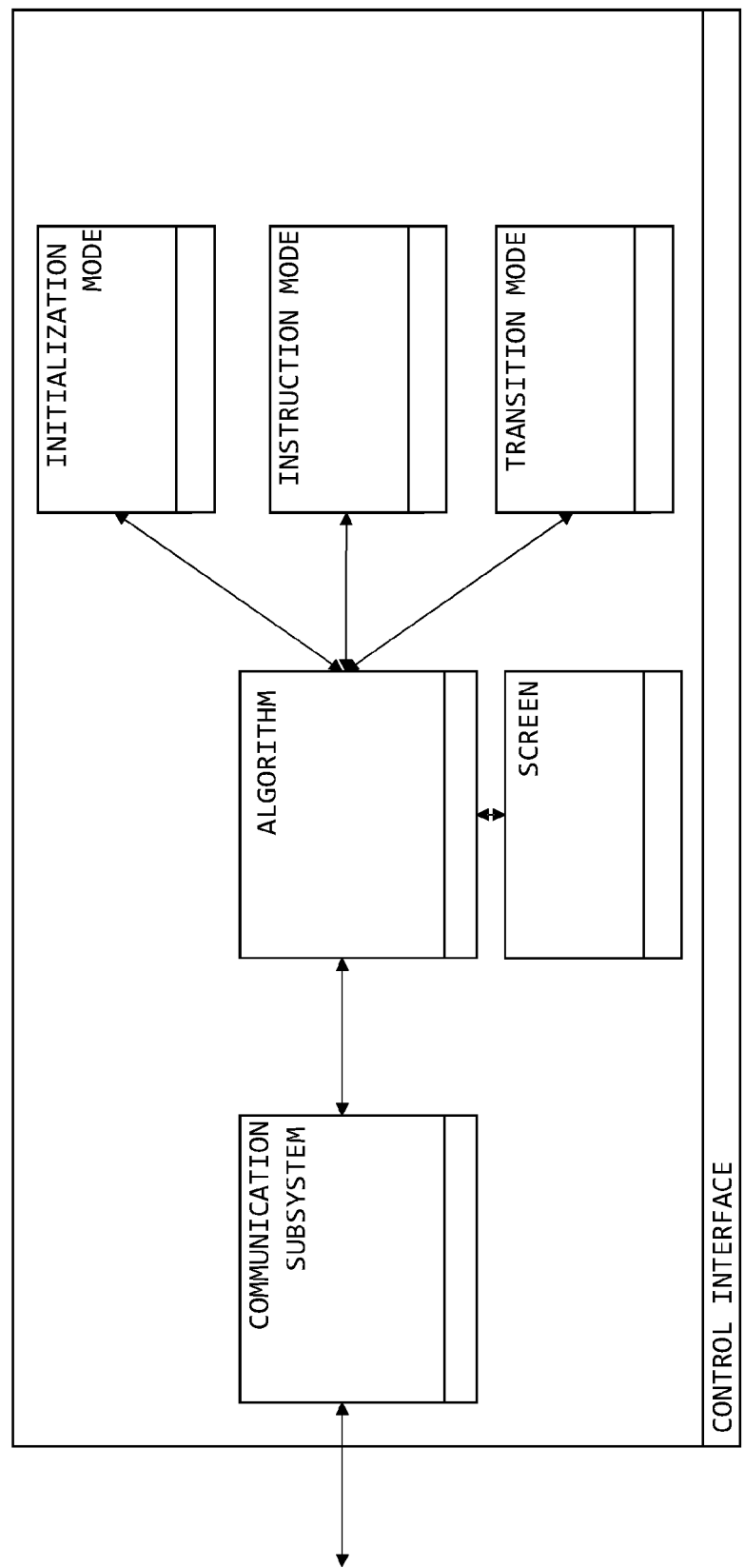
FIGS. 8-12 illustrate an installation mode routine according to an embodiment of the invention.

In FIG. 8 is the configuration step of the control architecture. In this embodiment, the system boots into a screen asking the user to enter initialization mode. The device has a custom application running which hosts the necessary algorithms for installation of this system.

Figure 9:
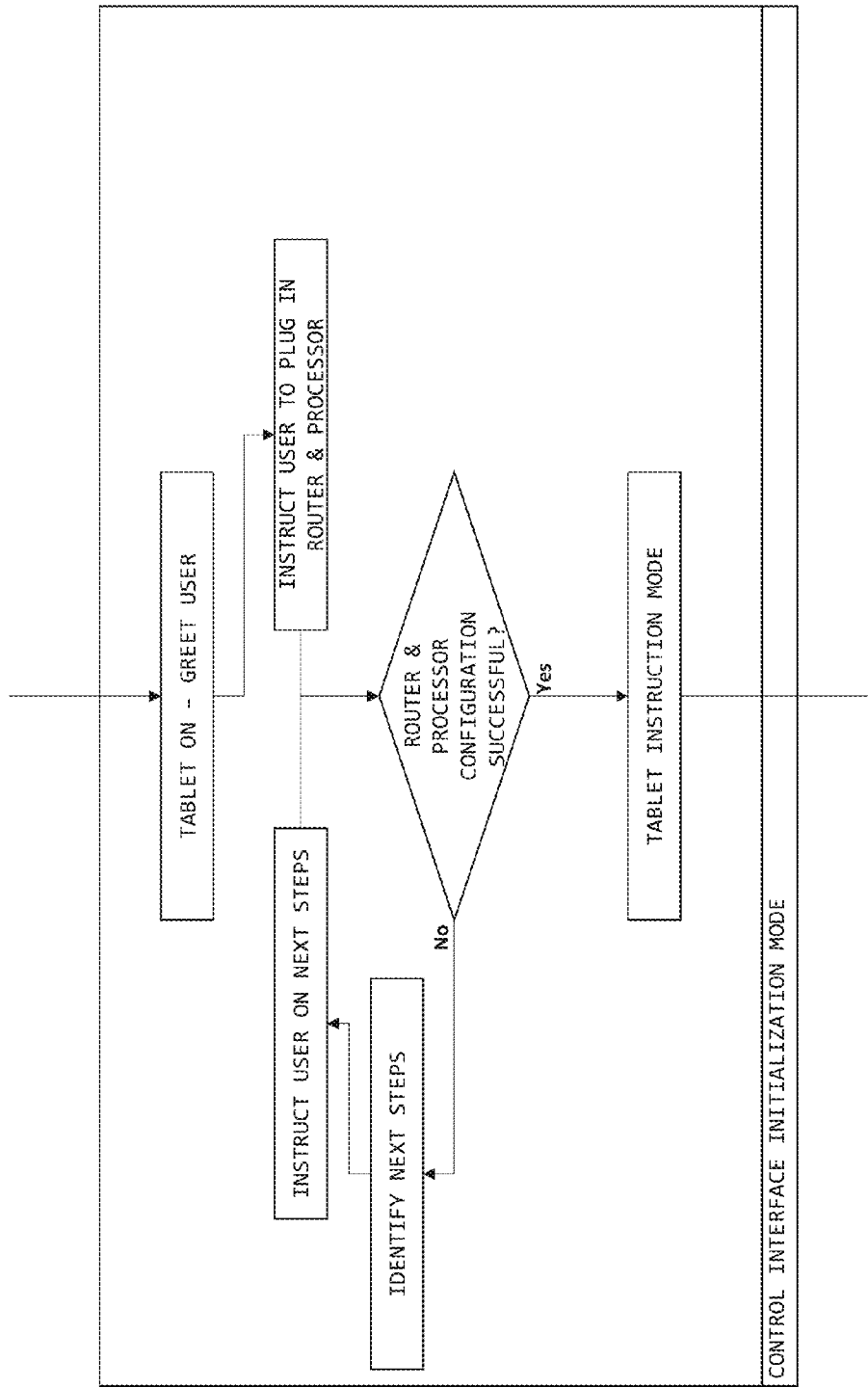
Figure 10:
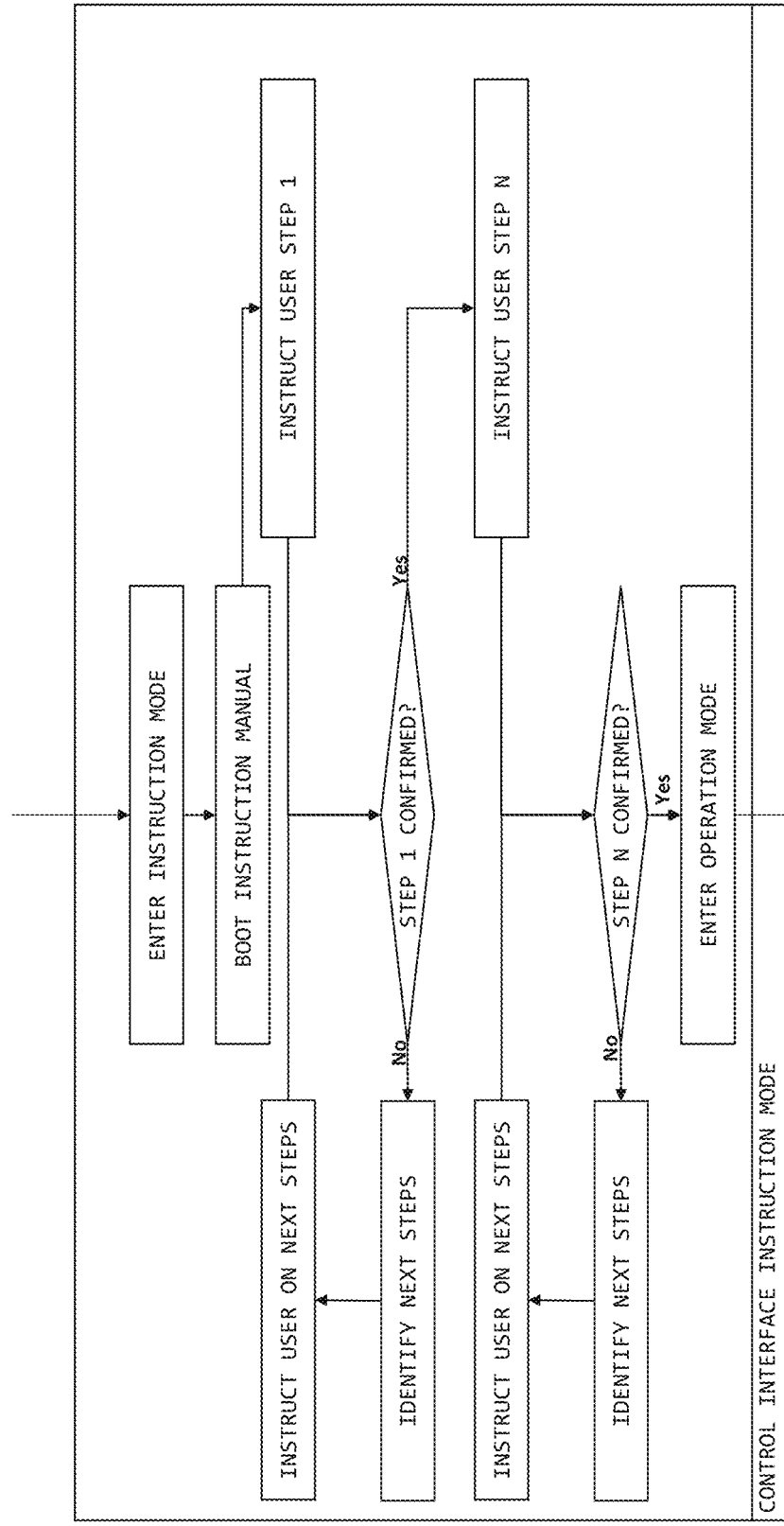

FIG. 9 describes the Initialization mode, where in this embodiment, the tablet is turned on and it greets the user. It then instructs the user to set up the wireless network or plug in the Router & Processor in this case. Once it is set up, the tablet confirms that the configuration was successful and enters the instruction mode. If the configuration was not successful, the router identifies the next steps, then instructs the user to execute them and tests the configuration again. Once the configuration is confirmed, the tablet enters the instruction mode.

Figure 11:
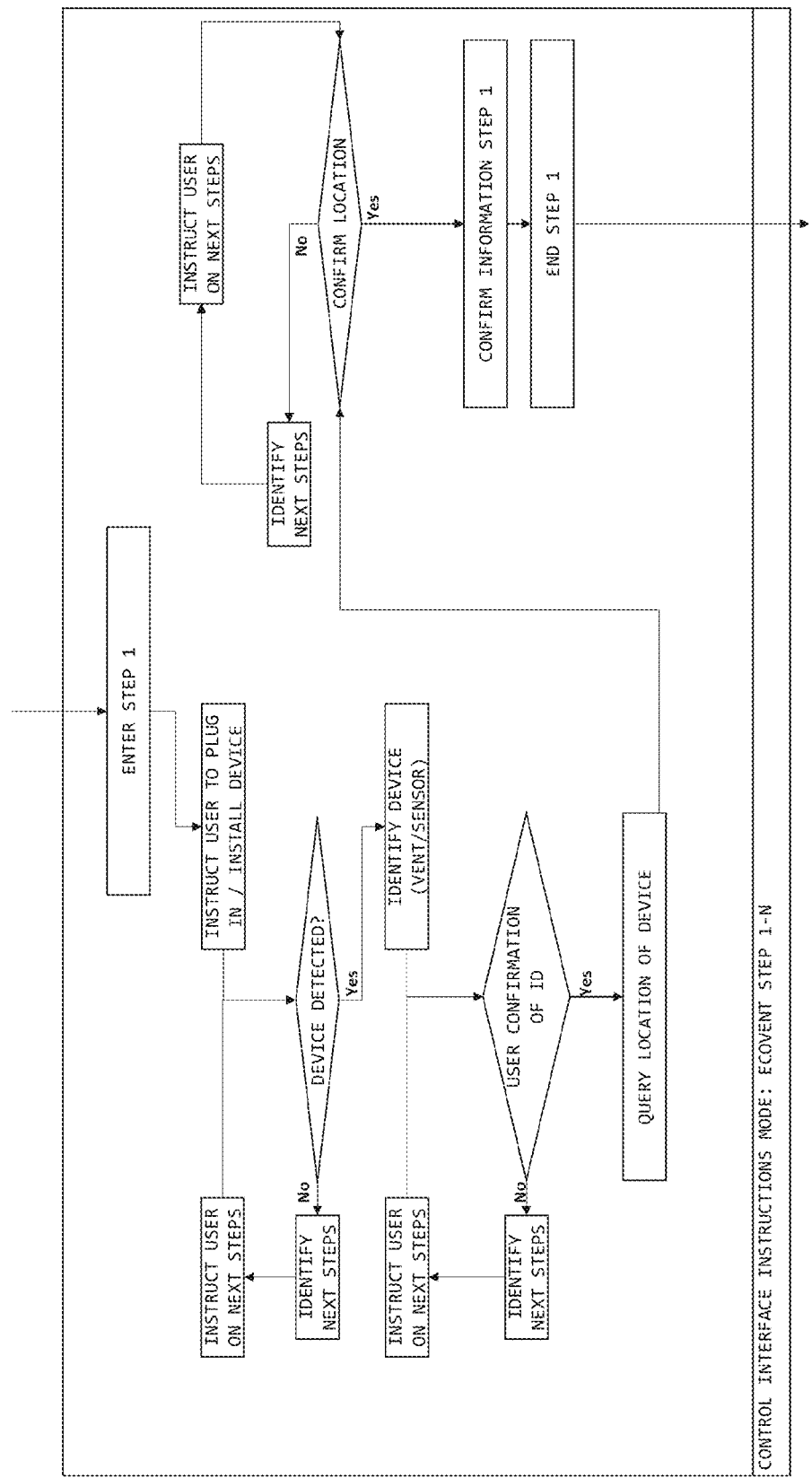
Figure 12:
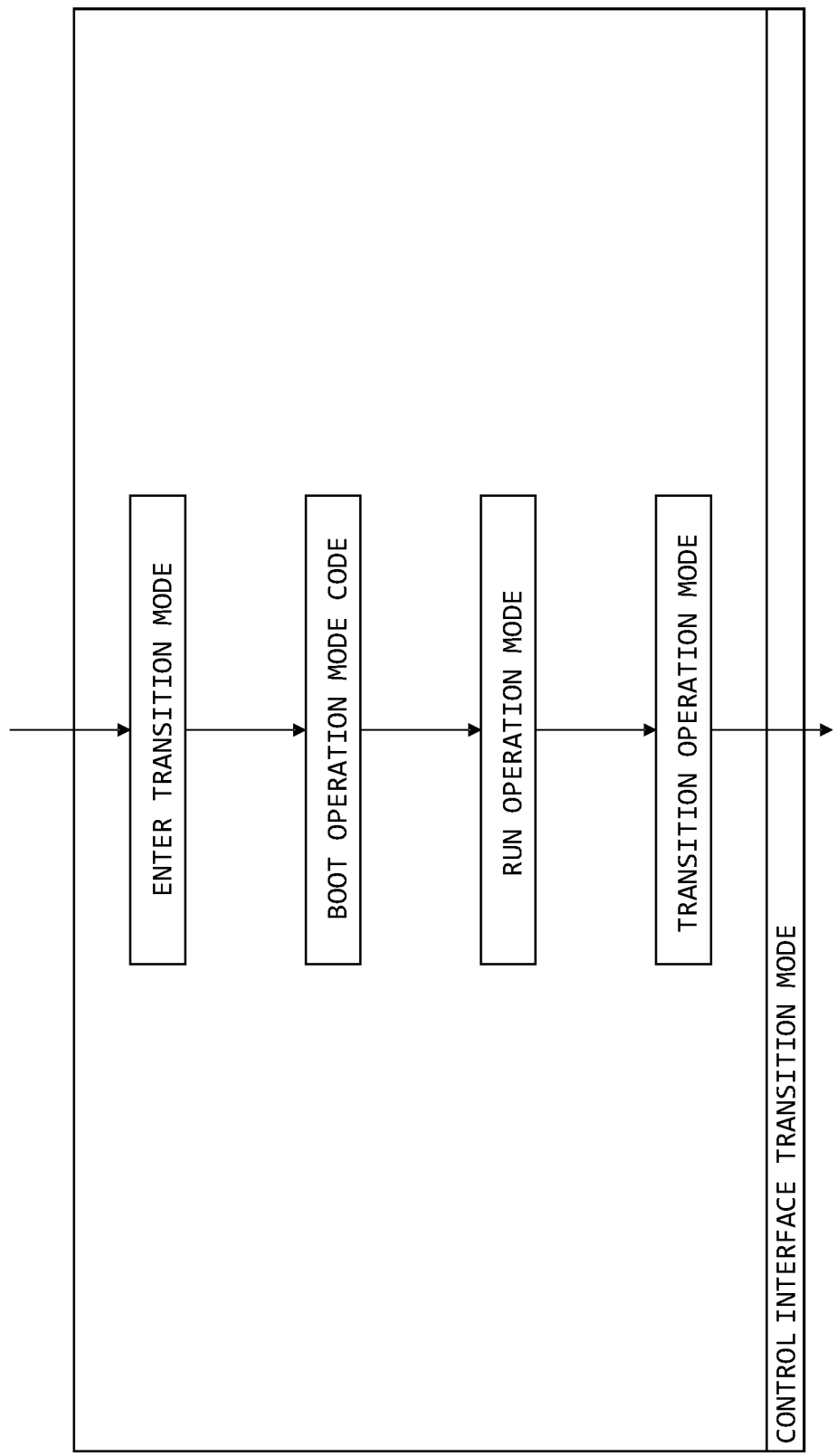

In this embodiment, the instruction mode (FIG. 10) boots the instruction manual, or in this case a specific set of software, and enter step 1 (as described in FIG. 11). It then confirms step 1. If successful it moves to the next step, if not, it selects the applicable course of action, and instruct the user on those steps. It then retries the confirmation of step 1.

In this embodiment, FIG. 11 describes the logic behind each Step (in this case Step 1). The system enters Step 1, as defined in FIG. 10, the Control Interface instructs the user to plug in one of the other devices (such as a vent, or sensor platform). It then attempts to detect the device and if successful, identify the device. If the detection is unsuccessful, the system determines the correct course, instruct the user and try the detection again.

In this implementation, after the device is detected, the system identifies the type of device, and confirms with the user. If the confirmation matches, the system then moves to location. If it doesn't match, the system identifies the next steps, instructs the user then tries to confirm the identification again.

In this embodiment after the device is identified and confirmed, the system queries the user about the location of the device. The user enters the location, and the system confirms. If the confirmation is accepted, the system ends step 1 and returns to FIG. 10. If it is not accepted, the system determines the best next steps, and instructs the user, then confirms the location again.

Once Step 1 is confirmed, it repeats this process for every step defined in the instruction manual, until all steps are confirmed. It then moves into the operation mode as defined in step 13.

Once in operation mode the control interface switches to the operational interface behave as a control device as described previously, until further installation of devices is necessary.

Figure 22:
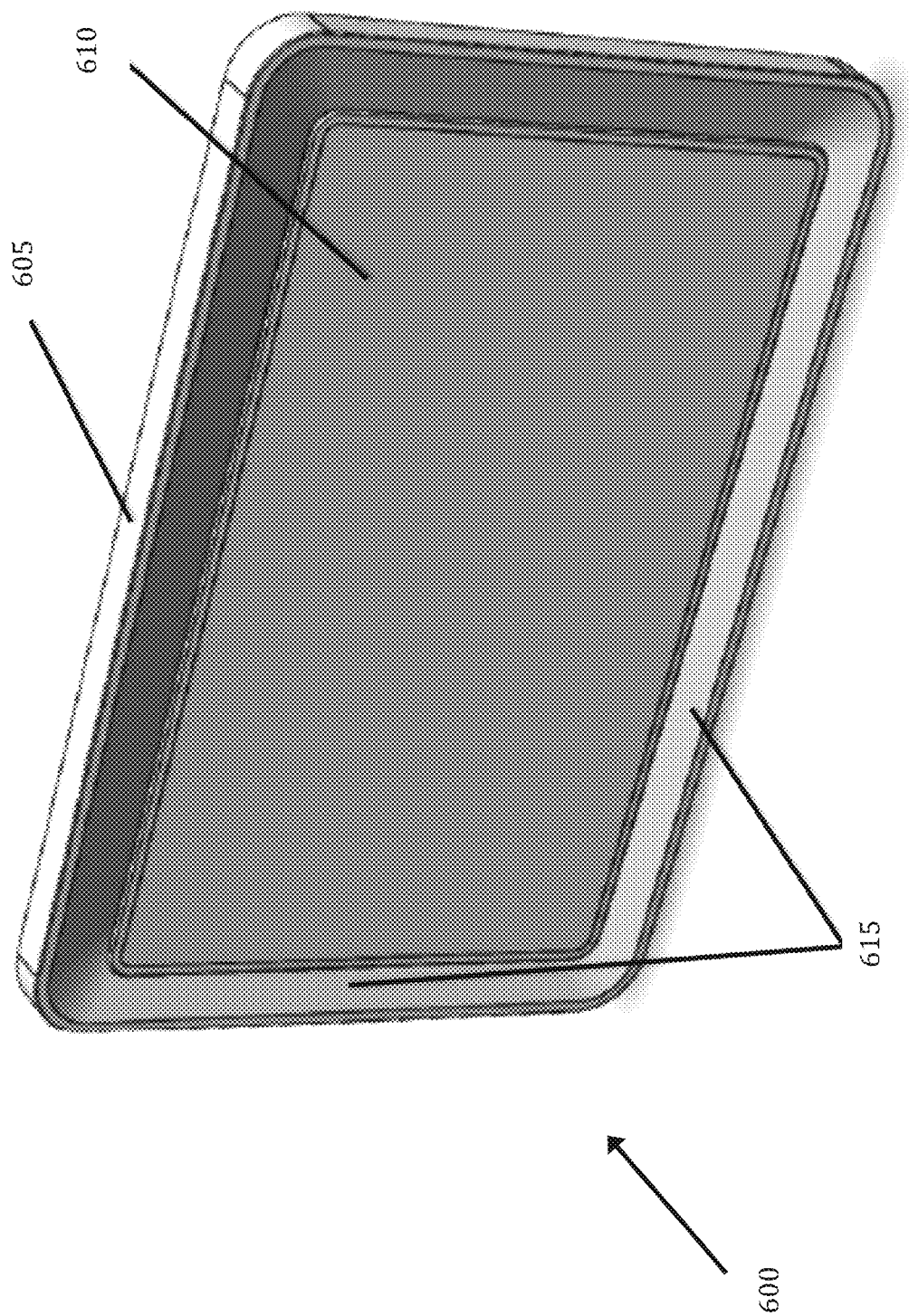
FIG. 22 illustrates a front perspective view of a faceplate assembly according to an embodiment of the invention.
Figure 23:
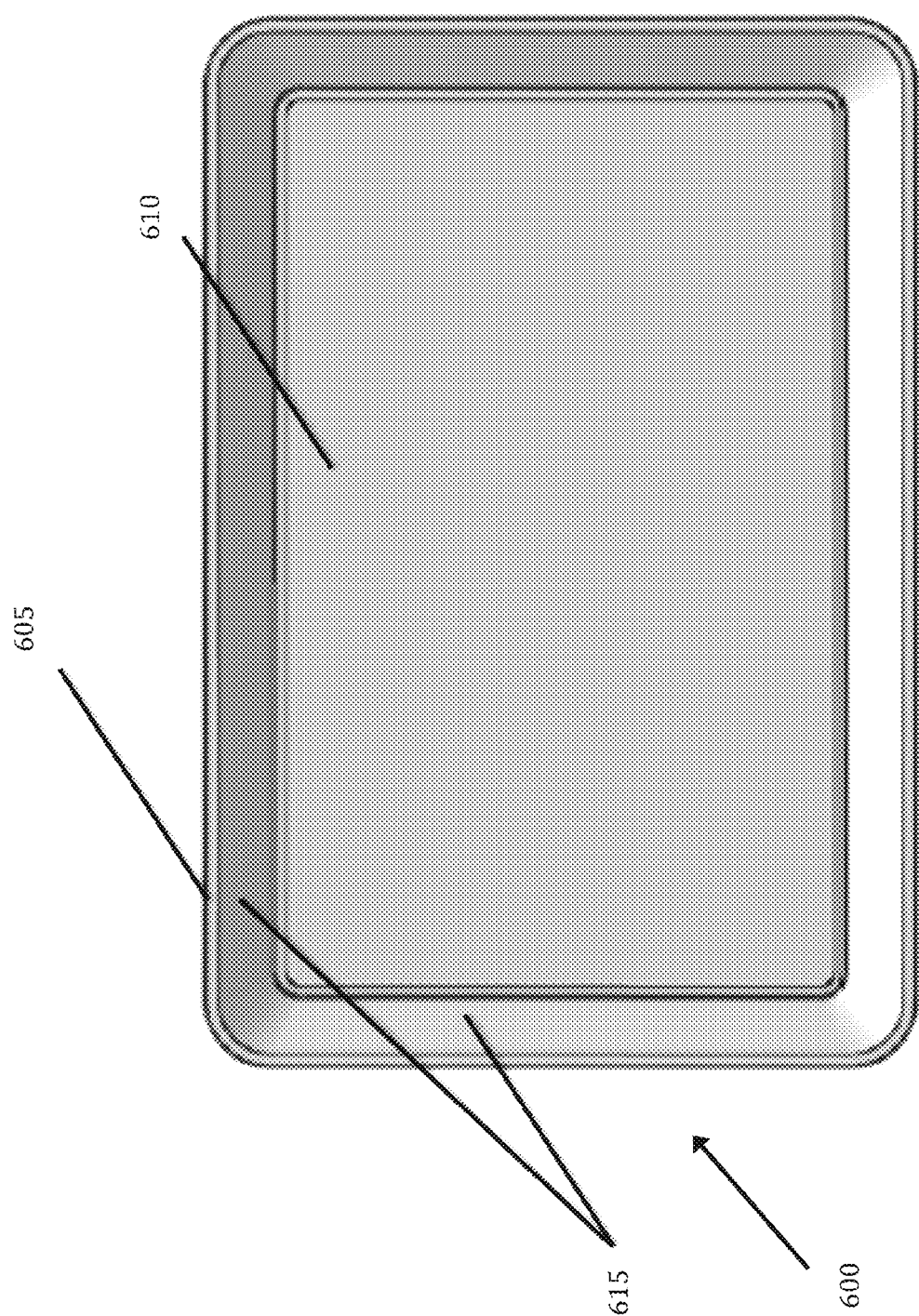
FIG. 23 illustrates a front view of a faceplate assembly according to an embodiment of the invention.

FIG. 22 illustrates a front perspective view of a faceplate assembly 600 according to an embodiment of the invention. The faceplate assembly 600 has a bezel 605 and a deflector plate 610. The deflector plate 610 is spaced apart from the bezel 605 to define an annular passage 615 between the space behind the faceplate and the space in front of the faceplate. FIG. 23 illustrates a front view of the faceplate assembly 600.

Figure 24:
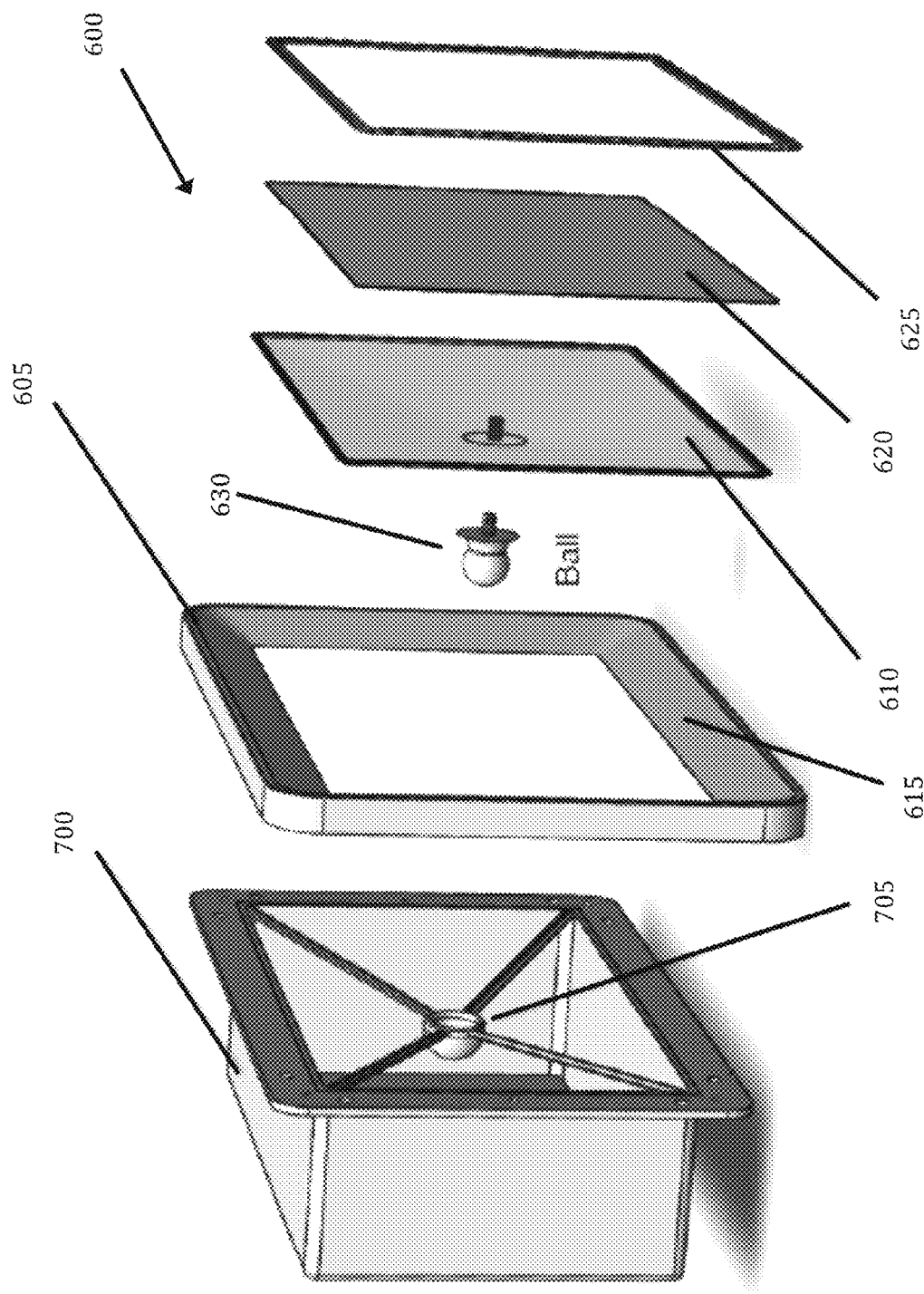
FIG. 24 illustrates an exploded perspective view of a housing and faceplate assembly according to an embodiment of the invention.

FIG. 24 illustrates an exploded perspective view of a housing 700 and the faceplate assembly 600 according to an embodiment of the invention. FIG. 24 shows the deflector plate 610 separate from the bezel, revealing an angled bevel 615 of the deflector plate 610. The figure also shows an optional interchangeable inlay plate 620, which can impart a decorative aspect to the deflector plate 610. The figure also shows an optional edge material 625, which is applied to the deflector plate 610 and surrounds the edge of the deflector plate (described in more detail below).

Figure 25:
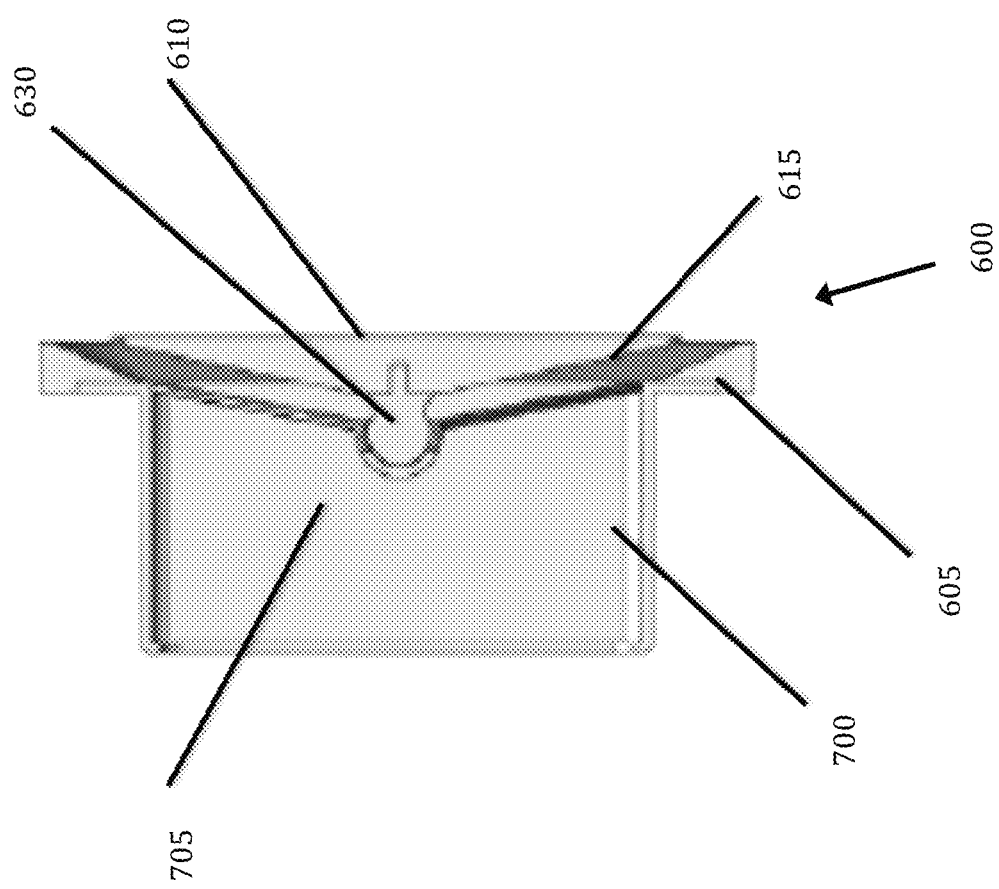
FIG. 25 illustrates a cross-sectional side view of a housing and faceplate assembly according to an embodiment of the invention.
Figure 26:
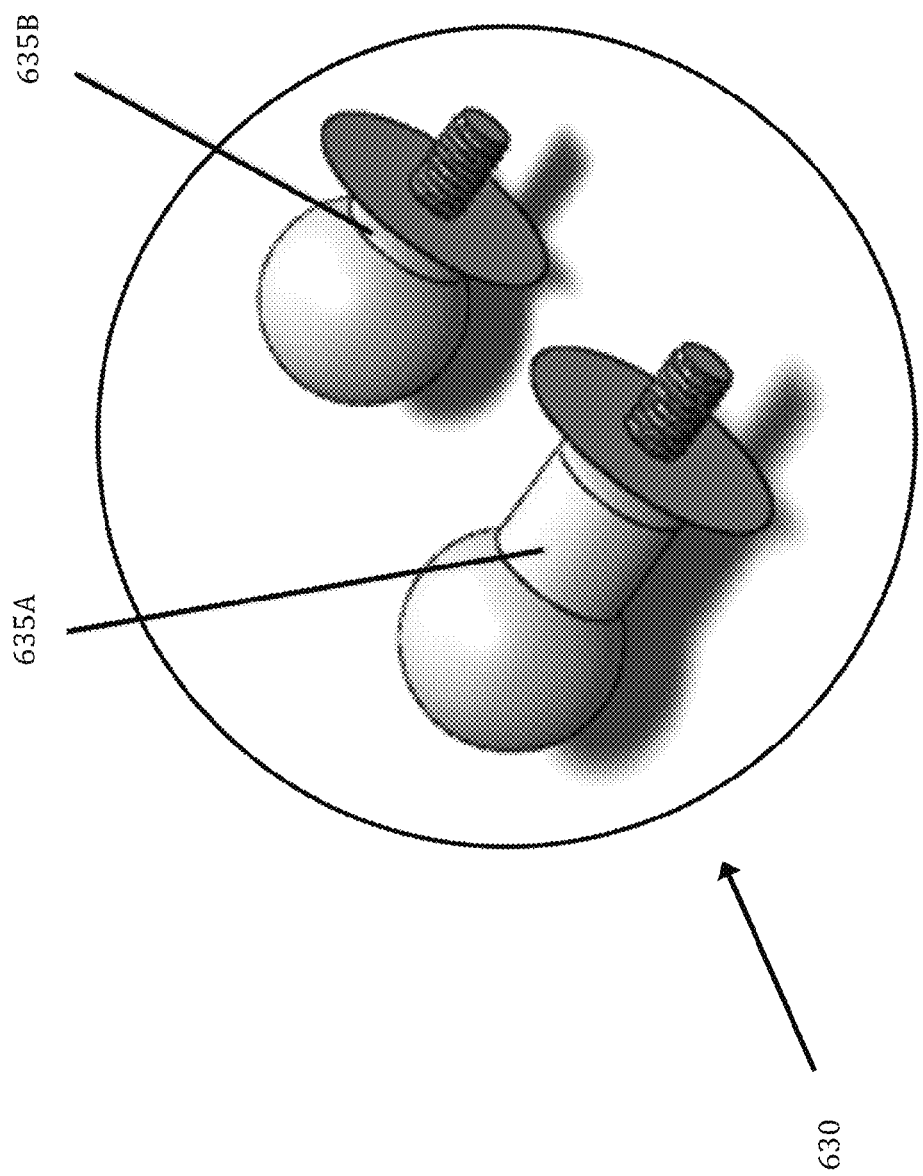
FIG. 26 illustrates a perspective view of two ball pins according to an embodiment of the invention.

A ball pin 630 is removably attached to the back surface of the deflector plate 610. The ball pin 630 fits into socket 705 that is part of the housing 700. The ball pin 630 and socket 705 cooperate to hold the deflector plate 610 apart from the bezel 605. FIG. 25 illustrates a cross-sectional side view of the housing 700 and the faceplate assembly 600. This figure shows the cooperation between the socket 705 of the housing and ball pin 630 attached to the deflector plate 610 that provides the spacing to define the annular passage 615. In addition, this figure illustrates how the bezel 605 is attached to the housing 700. As described above, the bezel can be magnetically mounted to the housing or by using known methods of attachment, such as screws, adhesives, or clips that attach to the housing sides. FIG. 26 illustrates a perspective view of two ball pins 630 according to an embodiment of the invention. As shown in the figure, each ball pin has a neck portion 635. The ball pins are interchangeable and each can have a neck portions of different lengths. In one implementation of the ball pin 630, the length of neck portion 635A is relatively long, while in another implementation, the length of neck portion 635B is relatively short. Ball pins with relatively longer neck portions will define relatively larger annular passages 615 as compared to ball pins having relatively shorter neck portions.

Figure 27:
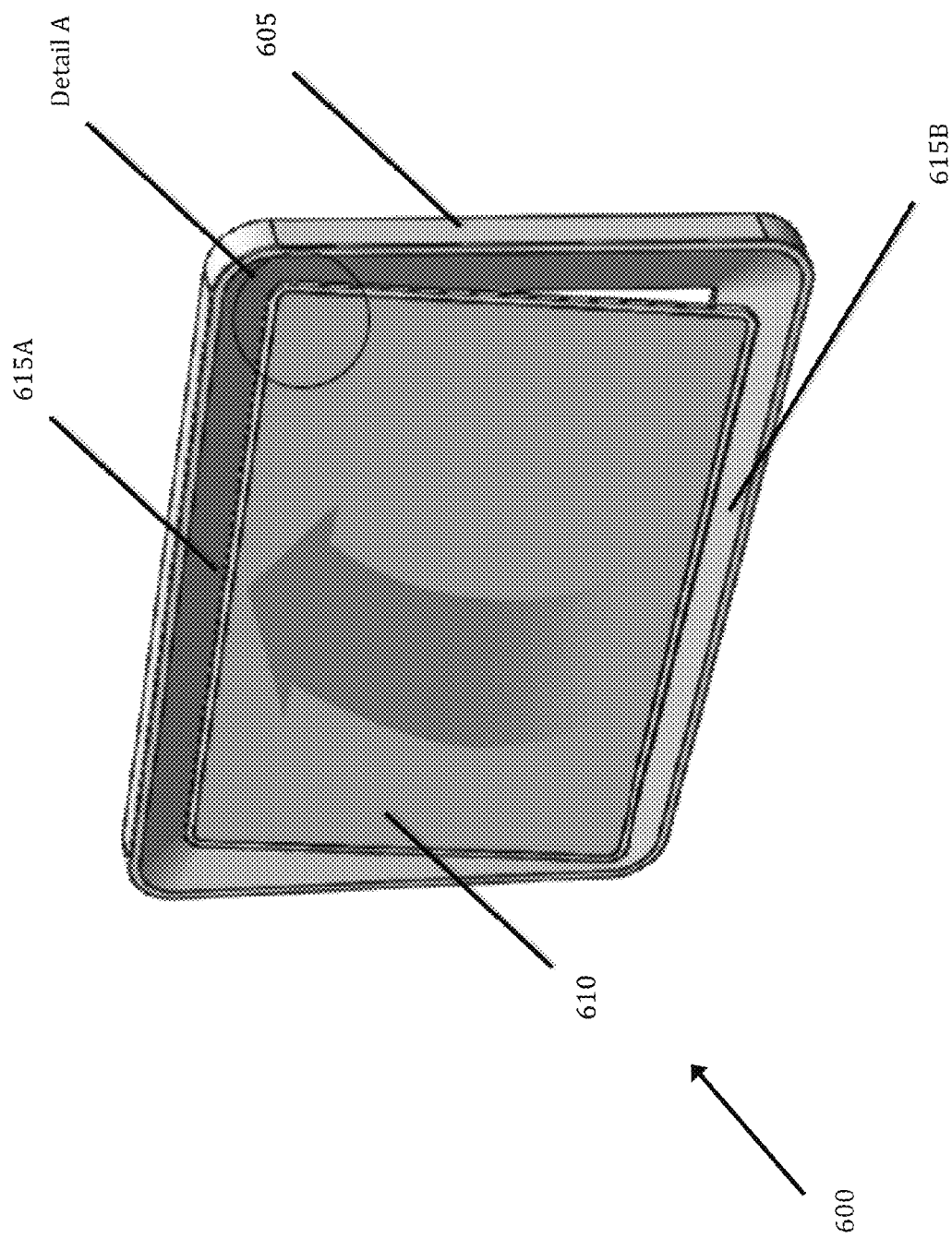
FIG. 27 illustrates a front perspective view of a faceplate assembly according to an embodiment of the invention.

FIG. 27 illustrates a front perspective view of the faceplate assembly 600. The ball pin and socket form a joint that enables the deflector plate 610 to be tilted relative to the bezel 605. When the deflector plate 610 is held substantially flat relative to the bezel plane, the annular passage 615 is open on all four edges of the bezel. This forms a 4-way vent that distributes air flowing through the annular passage in all four directions. When the deflector plate 610 is tilted upwards, the top edge of the deflector plate 610 contacts the top bevel of the bezel 605, thereby sealing off the top portion of the annular passage 615A. Meanwhile, the bottom portion of the annular passage 615B is opened more widely. In this way, the faceplate assembly 605 forms a directional vent when coupled to a housing present in the ductwork of an HVAC system. A user can direct air in the desired direction using the vent. In a rectangular implementation, tilting the deflector plate 610 towards its long edge creates a vent that directs air in predominately one direction (a 1-way vent), while tilting the deflector plate towards its short edge creates a vent that directs air in predominately three directions (a 3-way vent). Although only a rectangular implementation is shown and described, other shapes, such as square, circular, oval, triangular, and polygonal are within the scope of the invention.

Figure 28:
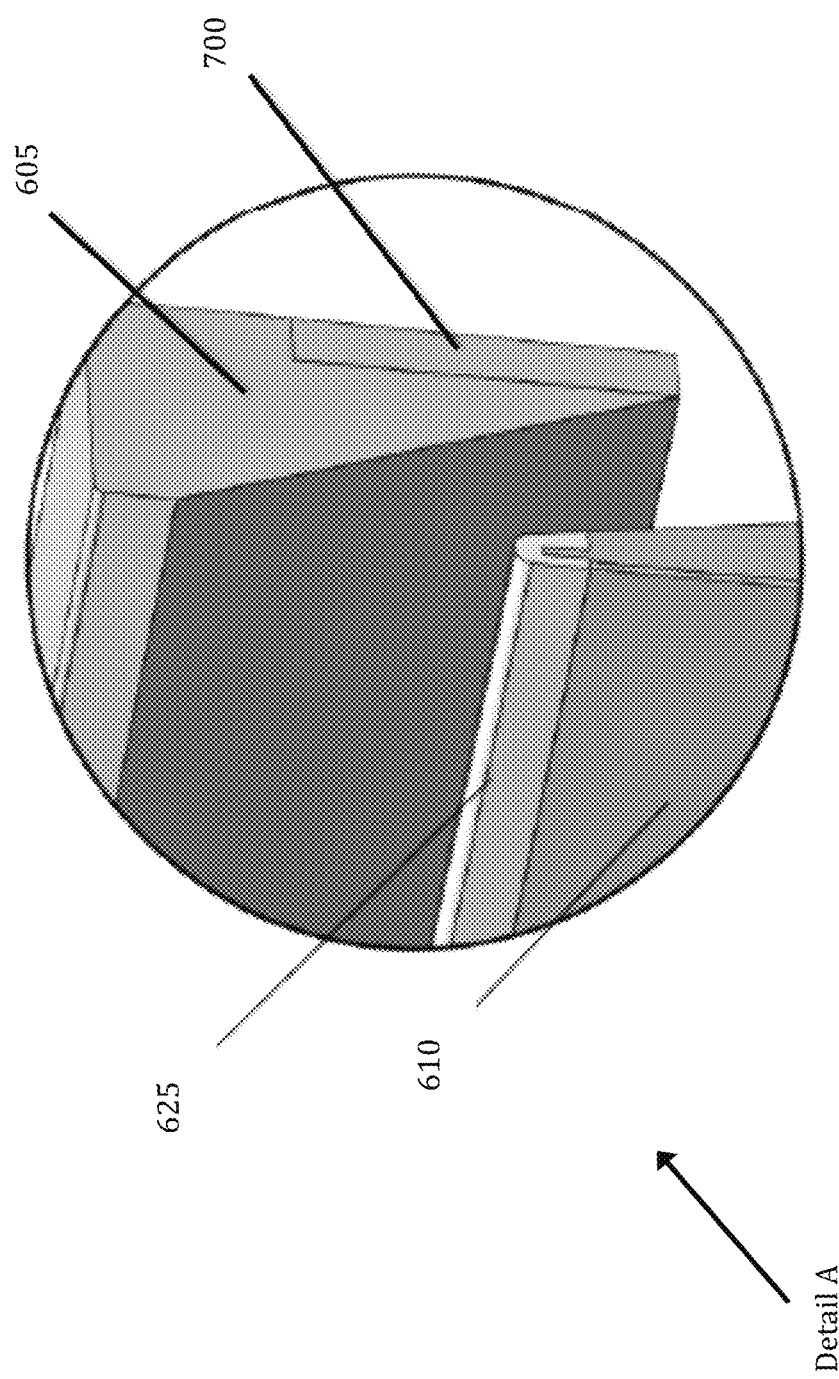
FIG. 28 illustrates detail A of FIG. 27.

FIG. 28 illustrates Detail A of FIG. 27. As mentioned above, an implementation of deflector plate 610 has optional edge material 625. Edge material 625 can be rubber, silicone, or any other pliable and resilient material to help create a seal between the edge of the deflector plate and the bevel of the bezel 605. Detail A also shows the mounting of the bezel 605 to the housing 700.

Embodiments of the faceplate assembly 600 offer less resistance to airflow than known vent/register faceplates. For example, simulations of the faceplate assembly attached to a housing of about 6 inches by 10 inches with a two-piece variable shutter mechanism were performed. The 1-way faceplates were modelled using a scoop design that directed air in predominately one direction. When compared to stamped steel register faceplates, the simulated faceplate assembly shows at least about a 25% less pressure drop at a flow rate of 98 cubic feet per minute at a velocity of 500 feet per minute (0.057 inches of water versus 0.076 inches of water). Meanwhile, simulations of the faceplate assembly compared to stamped steel register faceplates shows at least about an 8% less pressure drop at a flow rate of 208 cubic feet per minute at a velocity of 500 feet per minute (0.374 inches of water versus 0.409 inches of water). It is expected that some embodiments of the faceplates described herein will have at least about 5% less pressure drop compared to stamped steel register faceplates. Other embodiments are expected to have at least about 10% less pressure drop compared to stamped steel register faceplates. While still other embodiments are expected to have at least about 15% less pressure drop compared to stamped steel register faceplates. Still further embodiments are expected to have at least about 20% less pressure drop compared to stamped steel register faceplates. Other embodiments are expected to have at least about 30% less pressure drop compared to stamped steel register faceplates.

Embodiments of the faceplate assembly 600 also produce less noise than known vent faceplates and are believed to encourage a more laminar flow condition than known vent faceplates. For example, simulations of noise produced by the 6 inch by 10 inch model faceplate assembly described were performed. When compared to stamped steel register faceplates, the simulated faceplate assembly shows at least about 11.8% less pressure noise at a nominal flow rate (75 decibels versus 85 decibels). It is expected that some embodiments of the faceplates described herein will produce at least about 5% less noise compared to stamped steel register faceplates. Other embodiments are expected to produce at least about 10% less noise compared to stamped steel register faceplates. While still other embodiments are expected to produce at least about 15% less noise compared to stamped steel register faceplates. Still further embodiments are expected to produce at least about 20% less noise compared to stamped steel register faceplates. Other embodiments are expected to produce at least about 25% less noise compared to stamped steel register faceplates. The percentage reductions of noise recited herein are intended as percentage reductions of decibel values.

Certain aspects of the techniques and systems disclosed herein may be implemented as a computer program product for use with a computer system or computerized electronic device. Such implementations may include a series of computer instructions, or logic, fixed either on a tangible medium, such as a computer readable medium (e.g., a diskette, CD-ROM, ROM, flash memory or other memory or fixed disk) or transmittable to a computer system or a device, via a modem or other interface device, such as a communications adapter connected to a network over a medium.

The medium may be either a tangible medium (e.g., optical or analog communications lines) or a medium implemented with wireless techniques (e.g., Wi-Fi, cellular, microwave, infrared or other transmission techniques). The series of computer instructions embodies at least part of the functionality described herein with respect to the system. Those skilled in the art should appreciate that such computer instructions can be written in a number of programming languages for use with many computer architectures or operating systems.

Furthermore, such instructions may be stored in any tangible memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Preferred embodiments of the invention are described above as having communications, routing, and processing functions located in various components of the system. For example, the sensor platform 201 can act as a repeater for other system components. However, these functions can be distributed in other components of the system and remain within the scope of the invention. Thus, for example, vents can communicate directly with a thermostat, a control interface, or any other system component. Likewise, the determination of operating parameters that is described as being performed by one particular component can be performed by another component.

What is claimed is:

1. A sensor system comprising:
a plurality of sensor assemblies disposed in a building, each sensor assembly comprising:
a temperature sensor for sensing the ambient temperature of the space in the building within which the sensor is placed,
a pressure sensor for sensing the ambient pressure of the space in the building within which the sensor is placed, and
a sensor communication system for transmitting and receiving information; and
a sensor information aggregator that receives information about the ambient temperatures and ambient pressures in the building sensed from the sensors of the plurality of sensor assemblies, the sensor information aggregator comprising:
an aggregator communication system for transmitting and receiving information, and
an aggregator processor system for determining a vertical spatial temperature gradient in the building based on the information about the ambient temperatures in the building and ambient pressures in the building received by the sensor information aggregator, wherein the vertical spatial temperature gradient represents a change in temperature as a function of a change in altitude; and
wherein the aggregator processor system uses wireless communication signal strength between the sensor information aggregator and the sensor assemblies to estimate sensor assembly locations relative to each other, the determination of the vertical spatial temperature gradient in the building being further based on the relative locations of the sensor assemblies.

2. The sensor system of claim 1, at least one of the plurality of sensor assemblies being wall-mounted.

3. The sensor system of claim 1, at least one of the plurality of sensor assemblies being portable and carried by an individual.

4. The sensor system of claim 1, wherein the aggregator processor system uses manually entered locations of sensor assembly locations relative to each other, the determination of the vertical spatial temperature gradient in the building being further based on the relative locations of the sensor assemblies.

* * * * *